US012661365B2

(12) United States Patent
Li et al.

(10) Patent No.: US 12,661,365 B2
(45) Date of Patent: Jun. 23, 2026

(54) USE OF CANNABIDIOL IN THE TREATMENT OF EPILEPSY

(71) Applicant: Jazz Pharmaceuticals Research UK Limited, Sittingbourne (GB)

(72) Inventors: Jie Li, Carlsbad, CA (US); Kevin James Craig, Sittingbourne (GB); Daniel Adam Checketts, Sittingbourne (GB); David John Critchley, Sittingbourne (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 465 days.

(21) Appl. No.: 18/002,437

(22) PCT Filed: Jun. 16, 2021

(86) PCT No.: PCT/GB2021/051520

§ 371 (c)(1),
(2) Date: Dec. 19, 2022

(87) PCT Pub. No.: WO2021/255446

PCT Pub. Date: Dec. 23, 2021

(65) Prior Publication Data

US 2023/0225986 A1 Jul. 20, 2023

(30) Foreign Application Priority Data

Jun. 18, 2020 (GB) ..................................... 2009321

(51) Int. Cl.
*A61K 31/00* (2006.01)
*A61K 31/522* (2006.01)

(52) U.S. Cl.
CPC .......... *A61K 31/658* (2023.05); *A61K 31/522* (2013.01)

(58) Field of Classification Search
CPC ............................ A61K 31/658; A61K 31/522
See application file for complete search history.

(56) References Cited

U.S. PATENT DOCUMENTS

| | | | |
|---|---|---|---|
| 2,304,669 | A | 12/1942 | Adams |
| 6,383,513 | B1 | 5/2002 | Watts et al. |
| 6,403,126 | B1 | 6/2002 | Webster |
| 6,949,582 | B1 | 9/2005 | Wallace |
| 7,025,992 | B2 | 4/2006 | Whittle et al. |
| 8,222,292 | B2 | 7/2012 | Goskonda et al. |
| 8,293,786 | B2 | 10/2012 | Stinchcomb |
| 8,603,515 | B2 | 12/2013 | Whittle |
| 8,632,825 | B2 | 1/2014 | Velasco Diez et al. |
| 8,673,368 | B2 | 3/2014 | Guy et al. |
| 8,790,719 | B2 | 7/2014 | Parolaro et al. |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,095,554 | B2 | 8/2015 | Lewis et al. |
| 9,095,555 | B2 | 8/2015 | Winnicki |
| 9,125,859 | B2 | 9/2015 | Whalley et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,477,019 | B2 | 10/2016 | Li et al. |
| 9,492,438 | B2 | 11/2016 | Pollard |
| 9,522,123 | B2 | 12/2016 | Whalley et al. |
| 9,630,941 | B2 | 4/2017 | Elsohly et al. |
| 9,675,654 | B2 | 6/2017 | Parolaro et al. |
| 9,680,796 | B2 | 6/2017 | Miller et al. |
| 9,730,911 | B2 | 8/2017 | Verzura et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS https://web.archive.org/web/20191220210719/https://greendoorcbd.com/blogs/news/how-does-caffeine-affect-cbd.*
U.S. Appl. No. 62/004,495, filed May 29, 2014, Vangara et al.
U.S. Appl. No. 61/969,070, filed Mar. 21, 2014, Kane et al.
U.S. Appl. No. 14/724,351, filed May 28, 2015, Vangara et al.
Notice of Opposition to European Patent Application No. EP15784111.5, Patent No. EP3206716, dated May 10, 2021, 25 pages.
Adams, R. et al., "Isolation of Cannabinol, Cannabidiol and Quebrachitol from Red Oil of Minnesota Wild Hemp," J. Am. Chem. Soc. 1940, 62, 8, 2194-2196.
Afinitor® (everolimus) tablets, for oral use, and Afinitor Disperz® (everolimus tablets for oral suspension) Prescribing Information, 2009, 49 pages.

(Continued)

*Primary Examiner* — Shirley V Gembeh
(74) *Attorney, Agent, or Firm* — COOLEY LLP

(57) ABSTRACT

The present invention relates to the use of cannabidiol (CBD) in the treatment of patients with childhood-onset epilepsy who are concurrently taking caffeine. Where the CBD is used in combination with caffeine, caution should be taken. For example, the dose of either the CBD and/or caffeine may be required to be reduced. Moreover, the patient may need to be monitored for side effects of said drug-drug interaction. Preferably the CBD used is in the form of a highly purified extract of *cannabis* such that the CBD is present at greater than 95% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

21 Claims, 6 Drawing Sheets

(56) References Cited

U.S. PATENT DOCUMENTS

| | | | |
|---|---|---|---|
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado |
| 10,226,433 | B2 | 3/2019 | DiMarzo et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy et al. |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |
| 10,849,860 | B2 | 12/2020 | Guy et al. |
| 10,918,608 | B2 | 2/2021 | Guy et al. |
| 10,925,525 | B2 | 2/2021 | Nakaji |
| 10,966,939 | B2 | 4/2021 | Guy et al. |
| 11,000,486 | B2 | 5/2021 | Liu et al. |
| 11,065,209 | B2 | 7/2021 | Guy et al. |
| 11,065,227 | B2 | 7/2021 | Stott et al. |
| 11,096,905 | B2 | 8/2021 | Guy et al. |
| 11,147,776 | B2 | 10/2021 | Stott et al. |
| 11,147,783 | B2 | 10/2021 | Stott et al. |
| 11,154,516 | B2 | 10/2021 | Guy et al. |
| 11,154,517 | B2 | 10/2021 | Guy et al. |
| 11,160,757 | B1 | 11/2021 | Wilkhu et al. |
| 11,160,795 | B2 | 11/2021 | Guy et al. |
| 11,207,292 | B2 | 12/2021 | Guy et al. |
| 11,224,660 | B2 | 1/2022 | Vangara et al. |
| 11,229,612 | B2 | 1/2022 | Wright et al. |
| 11,291,631 | B2 | 4/2022 | Shah |
| 11,311,498 | B2 | 4/2022 | Guy et al. |
| 11,318,109 | B2 | 5/2022 | Whalley et al. |
| 11,331,279 | B2 | 5/2022 | Vangara et al. |
| 11,357,741 | B2 | 6/2022 | Guy et al. |
| 11,400,055 | B2 | 8/2022 | Guy et al. |
| 11,406,623 | B2 | 8/2022 | Guy et al. |
| 11,413,266 | B2 | 8/2022 | Biro et al. |
| 11,419,829 | B2 | 8/2022 | Whalley et al. |
| 11,426,362 | B2 | 8/2022 | Wright et al. |
| 11,446,258 | B2 | 9/2022 | Guy et al. |
| 11,590,087 | B2 | 2/2023 | Guy et al. |
| 11,633,369 | B2 | 4/2023 | Guy et al. |
| 11,679,087 | B2 | 6/2023 | Guy et al. |
| 11,684,598 | B2 | 6/2023 | Stott et al. |
| 11,701,330 | B2 | 7/2023 | Guy et al. |
| 11,709,671 | B2 | 7/2023 | Joubert et al. |
| 11,766,411 | B2 | 9/2023 | Guy et al. |
| 11,793,770 | B2 | 10/2023 | Stott et al. |
| 11,806,319 | B2 | 11/2023 | Wilkhu et al. |
| 11,865,102 | B2 | 1/2024 | Guy et al. |
| 11,963,937 | B2 | 4/2024 | Guy et al. |
| 12,023,305 | B2 | 7/2024 | Whalley et al. |
| 12,064,398 | B2 | 8/2024 | Wright et al. |
| 12,064,399 | B2 | 8/2024 | Guy et al. |
| 12,102,619 | B2 | 10/2024 | Guy et al. |
| 12,121,499 | B2 | 10/2024 | Whalley et al. |
| 12,161,607 | B2 | 12/2024 | Wright et al. |
| 12,213,985 | B2 | 2/2025 | Shah |
| 12,263,139 | B2 | 4/2025 | Whalley et al. |
| 12,318,356 | B2 | 6/2025 | Guy |
| 12,383,567 | B2 | 8/2025 | Guy et al. |
| 2004/0034108 | A1 | 2/2004 | Whittle |
| 2004/0049059 | A1 | 3/2004 | Mueller |
| 2004/0110828 | A1 | 6/2004 | Chowdhury et al. |
| 2004/0147767 | A1 | 7/2004 | Whittle et al. |
| 2005/0042172 | A1 | 2/2005 | Whittle |
| 2005/0266108 | A1 | 12/2005 | Flockhart et al. |
| 2006/0039959 | A1 | 2/2006 | Wessling |
| 2006/0167283 | A1 | 7/2006 | Flockhart et al. |
| 2007/0060638 | A1 | 3/2007 | Olmstead |
| 2007/0099987 | A1 | 5/2007 | Weiss et al. |
| 2007/0238786 | A1 | 10/2007 | Hobden et al. |
| 2008/0112895 | A1 | 5/2008 | Kottayil et al. |
| 2008/0119544 | A1 | 5/2008 | Guy et al. |
| 2008/0188461 | A1 | 8/2008 | Guan |
| 2009/0036523 | A1 | 2/2009 | Stinchcomb et al. |
| 2009/0264063 | A1 | 10/2009 | Tinsley et al. |
| 2009/0306221 | A1 | 12/2009 | Guy et al. |
| 2010/0239693 | A1 | 9/2010 | Guy et al. |
| 2010/0273895 | A1 | 10/2010 | Stinchcomb et al. |
| 2010/0317729 | A1 | 12/2010 | Guy et al. |
| 2011/0028431 | A1 | 2/2011 | Zerbe et al. |
| 2011/0033529 | A1 | 2/2011 | Samantaray et al. |
| 2011/0038958 | A1 | 2/2011 | Kikuchi et al. |
| 2011/0065747 | A1 | 3/2011 | Donello et al. |
| 2011/0082195 | A1 | 4/2011 | Guy et al. |
| 2011/0150825 | A1 | 6/2011 | Buggy et al. |
| 2011/0172262 | A1 | 7/2011 | Deftereos et al. |
| 2012/0004251 | A1 | 1/2012 | Whalley et al. |
| 2012/0165402 | A1 | 6/2012 | Whalley et al. |
| 2012/0183606 | A1 | 7/2012 | Bender et al. |
| 2012/0202891 | A1 | 8/2012 | Stinchcomb et al. |
| 2012/0270845 | A1 | 10/2012 | Bannister |
| 2013/0143894 | A1 | 6/2013 | Bergstrom et al. |
| 2013/0209483 | A1 | 8/2013 | McAllister |
| 2013/0245110 | A1 | 9/2013 | Guy et al. |
| 2013/0296398 | A1 | 11/2013 | Whalley et al. |
| 2014/0100269 | A1 | 4/2014 | Goskonda et al. |
| 2014/0155456 | A9 | 6/2014 | Whalley et al. |
| 2014/0243405 | A1 | 8/2014 | Whalley et al. |
| 2014/0335208 | A1 | 11/2014 | Cawthorne et al. |
| 2014/0343044 | A1 | 11/2014 | Ceulemens |
| 2015/0111939 | A1 | 4/2015 | Gruening et al. |
| 2015/0181924 | A1 | 7/2015 | Llamas |
| 2015/0320698 | A1 | 11/2015 | Whalley et al. |
| 2015/0335590 | A1 | 11/2015 | Whalley et al. |
| 2015/0342902 | A1 | 12/2015 | Vangara et al. |
| 2015/0343071 | A1 | 12/2015 | Vangara et al. |
| 2015/0359755 | A1 | 12/2015 | Guy et al. |
| 2015/0359756 | A1 | 12/2015 | Guy et al. |
| 2016/0010126 | A1 | 1/2016 | Poulos et al. |
| 2016/0166498 | A1 | 6/2016 | Anastassov |
| 2016/0166514 | A1 | 6/2016 | Guy et al. |
| 2016/0166515 | A1 | 6/2016 | Guy et al. |
| 2016/0220529 | A1 | 8/2016 | Guy et al. |
| 2016/0256411 | A1 | 9/2016 | Aung-Din |
| 2016/0317468 | A1 | 11/2016 | Sankar et al. |
| 2016/0338974 | A1 | 11/2016 | Aung-Din |
| 2017/0007551 | A1 | 1/2017 | Guy et al. |
| 2017/0008868 | A1 | 1/2017 | Dialer et al. |
| 2017/0172939 | A1 | 6/2017 | Guy et al. |
| 2017/0172940 | A1 | 6/2017 | Guy et al. |
| 2017/0172941 | A1 | 6/2017 | Guy et al. |
| 2017/0173043 | A1 | 6/2017 | Guy et al. |
| 2017/0173044 | A1 | 6/2017 | Guy et al. |
| 2017/0181982 | A1 | 6/2017 | Guy et al. |
| 2017/0224634 | A1 | 8/2017 | Vangara et al. |
| 2017/0231923 | A1 | 8/2017 | Guy et al. |
| 2017/0239193 | A1 | 8/2017 | Guy et al. |
| 2017/0246121 | A1 | 8/2017 | Guy et al. |
| 2017/0266126 | A1 | 9/2017 | Guy et al. |
| 2017/0273913 | A1 | 9/2017 | Wilkhu et al. |
| 2018/0028489 | A1 | 2/2018 | Vangara et al. |
| 2018/0071210 | A1 | 3/2018 | Wilkhu et al. |
| 2018/0228751 | A1 | 8/2018 | Stott et al. |
| 2018/0338931 | A1 | 11/2018 | Guy et al. |
| 2019/0031601 | A1 | 1/2019 | Elsohly et al. |
| 2019/0083418 | A1 | 3/2019 | Guy et al. |
| 2019/0091171 | A1 | 3/2019 | Guy et al. |
| 2019/0160393 | A1 | 5/2019 | Marshall et al. |
| 2019/0167583 | A1 | 6/2019 | Shah |
| 2019/0175547 | A1 | 6/2019 | Stott et al. |
| 2019/0247324 | A1 | 8/2019 | Whalley et al. |
| 2019/0314296 | A1 | 10/2019 | Wright et al. |
| 2019/0321307 | A1 | 10/2019 | Guy et al. |
| 2019/0365667 | A1 | 12/2019 | Wright et al. |
| 2020/0000741 | A1 | 1/2020 | Guy et al. |
| 2020/0069608 | A1 | 3/2020 | Guy et al. |

(56) References Cited

U.S. PATENT DOCUMENTS

| | | | |
|---|---|---|---|
| 2020/0138738 | A1 | 5/2020 | Guy et al. |
| 2020/0179303 | A1 | 6/2020 | Guy et al. |
| 2020/0206152 | A1 | 7/2020 | Stott et al. |
| 2020/0206153 | A1 | 7/2020 | Whalley et al. |
| 2020/0237683 | A1 | 7/2020 | Whalley et al. |
| 2020/0297656 | A1 | 9/2020 | Guy et al. |
| 2020/0323792 | A1 | 10/2020 | Guy et al. |
| 2020/0352878 | A1 | 11/2020 | Guy et al. |
| 2020/0368179 | A1 | 11/2020 | Guy et al. |
| 2021/0015789 | A1 | 1/2021 | Guy et al. |
| 2021/0052512 | A1 | 2/2021 | Guy et al. |
| 2021/0059949 | A1 | 3/2021 | Wilkhu et al. |
| 2021/0059960 | A1 | 3/2021 | Wilkhu et al. |
| 2021/0059976 | A1 | 3/2021 | Wilkhu et al. |
| 2021/0069333 | A1 | 3/2021 | Velasco Diez et al. |
| 2021/0093581 | A1 | 4/2021 | Guy et al. |
| 2021/0100755 | A1 | 4/2021 | Whalley et al. |
| 2021/0145765 | A1 | 5/2021 | Guy et al. |
| 2021/0167950 | A1 | 6/2021 | Arkko et al. |
| 2021/0169824 | A1 | 6/2021 | Guy et al. |
| 2021/0177773 | A1 | 6/2021 | Guy et al. |
| 2021/0196651 | A1 | 7/2021 | Guy et al. |
| 2021/0230145 | A1 | 7/2021 | Blankman et al. |
| 2021/0244685 | A1 | 8/2021 | Guy et al. |
| 2021/0290565 | A1 | 9/2021 | Guy et al. |
| 2021/0308072 | A1 | 10/2021 | Wright et al. |
| 2021/0330636 | A1 | 10/2021 | Guy et al. |
| 2021/0401771 | A1 | 12/2021 | Guy et al. |
| 2022/0000800 | A1 | 1/2022 | Guy et al. |
| 2022/0008355 | A1 | 1/2022 | Guy et al. |
| 2022/0016048 | A1 | 1/2022 | Guy et al. |
| 2022/0023232 | A1 | 1/2022 | Guy et al. |
| 2022/0040155 | A1 | 2/2022 | Guy et al. |
| 2022/0062197 | A1 | 3/2022 | Stott et al. |
| 2022/0062211 | A1 | 3/2022 | Stott et al. |
| 2022/0087951 | A1 | 3/2022 | Guy et al. |
| 2022/0096397 | A1 | 3/2022 | Wright et al. |
| 2022/0168266 | A1 | 6/2022 | Guy et al. |
| 2022/0183997 | A1 | 6/2022 | Guy et al. |
| 2022/0184000 | A1 | 6/2022 | Guy et al. |
| 2022/0202738 | A1 | 6/2022 | Guy et al. |
| 2022/0211629 | A1 | 7/2022 | Wilkhu et al. |
| 2022/0226257 | A1 | 7/2022 | Guy et al. |
| 2022/0233495 | A1 | 7/2022 | Silcock et al. |
| 2022/0249396 | A1 | 8/2022 | Guy et al. |
| 2022/0257529 | A1 | 8/2022 | Guy et al. |
| 2022/0265573 | A1 | 8/2022 | Guy et al. |
| 2022/0288055 | A1 | 9/2022 | Silcock et al. |
| 2022/0323375 | A1 | 10/2022 | Guy et al. |
| 2022/0362149 | A1 | 11/2022 | Shah |
| 2022/0378714 | A1 | 12/2022 | Guy et al. |
| 2022/0378715 | A1 | 12/2022 | Guy et al. |
| 2022/0378717 | A1 | 12/2022 | Guy et al. |
| 2022/0378738 | A1 | 12/2022 | Guy et al. |
| 2022/0387347 | A1 | 12/2022 | Whalley et al. |
| 2022/0395470 | A1 | 12/2022 | Whalley et al. |
| 2022/0395471 | A1 | 12/2022 | Guy et al. |
| 2023/0000789 | A1 | 1/2023 | Guy et al. |
| 2023/0022487 | A1 | 1/2023 | Guy et al. |
| 2023/0024312 | A1 | 1/2023 | Whalley et al. |
| 2023/0026079 | A1 | 1/2023 | Guy et al. |
| 2023/0032502 | A1 | 2/2023 | Guy et al. |
| 2023/0038423 | A1 | 2/2023 | Silcock et al. |
| 2023/0068885 | A1 | 3/2023 | Guy et al. |
| 2023/0143812 | A1 | 5/2023 | Knappertz et al. |
| 2023/0206209 | A1 | 6/2023 | Janiga |
| 2023/0235825 | A1 | 7/2023 | Thompson et al. |
| 2023/0248664 | A1 | 8/2023 | Guy et al. |
| 2023/0263744 | A1 | 8/2023 | Guy et al. |
| 2023/0277560 | A1 | 9/2023 | Checketts et al. |
| 2023/0277561 | A1 | 9/2023 | Checketts et al. |
| 2023/0277562 | A1 | 9/2023 | Checketts et al. |
| 2023/0277563 | A1 | 9/2023 | Checketts et al. |
| 2023/0285419 | A1 | 9/2023 | Checketts et al. |
| 2023/0285420 | A1 | 9/2023 | Checketts et al. |
| 2023/0285421 | A1 | 9/2023 | Checketts et al. |
| 2023/0285422 | A1 | 9/2023 | Checketts et al. |
| 2023/0285423 | A1 | 9/2023 | Checketts et al. |
| 2023/0285424 | A1 | 9/2023 | Checketts et al. |
| 2023/0285425 | A1 | 9/2023 | Checketts et al. |
| 2023/0285426 | A1 | 9/2023 | Checketts et al. |
| 2023/0285427 | A1 | 9/2023 | Checketts et al. |
| 2023/0285428 | A1 | 9/2023 | Checketts et al. |
| 2023/0301934 | A1 | 9/2023 | Whalley et al. |
| 2023/0301936 | A1 | 9/2023 | Guy et al. |
| 2023/0310464 | A1 | 10/2023 | Checketts et al. |
| 2023/0346809 | A1 | 11/2023 | Craig et al. |
| 2023/0372367 | A1 | 11/2023 | Checketts et al. |
| 2023/0372368 | A1 | 11/2023 | Checketts et al. |
| 2024/0016819 | A1 | 1/2024 | Craig et al. |
| 2024/0025858 | A1 | 1/2024 | Silcock et al. |
| 2024/0033229 | A1 | 2/2024 | Guy et al. |
| 2024/0043388 | A1 | 2/2024 | Silcock et al. |
| 2024/0050452 | A1 | 2/2024 | Craig et al. |
| 2024/0091241 | A1 | 3/2024 | Guy et al. |
| 2024/0130981 | A1 | 4/2024 | Wilkhu et al. |
| 2024/0131041 | A1 | 4/2024 | Tse et al. |
| 2024/0165048 | A1 | 5/2024 | Guy et al. |
| 2024/0207220 | A1 | 6/2024 | Guy et al. |
| 2024/0215910 | A1 | 7/2024 | Tse et al. |
| 2024/0226032 | A9 | 7/2024 | Wilkhu et al. |
| 2024/0226123 | A9 | 7/2024 | Tse et al. |
| 2024/0238218 | A1 | 7/2024 | Silcock et al. |
| 2024/0254066 | A1 | 8/2024 | Silcock et al. |
| 2024/0254072 | A1 | 8/2024 | Silcock et al. |
| 2024/0261234 | A1 | 8/2024 | Guy et al. |
| 2024/0293762 | A1 | 9/2024 | Loft et al. |
| 2024/0325416 | A1 | 10/2024 | Whitehouse |
| 2024/0350428 | A1 | 10/2024 | Guy et al. |
| 2024/0360060 | A1 | 10/2024 | Silcock et al. |
| 2025/0025482 | A1 | 1/2025 | Knappertz |
| 2025/0152521 | A1 | 5/2025 | Guy |
| 2025/0177321 | A1 | 6/2025 | Guy |
| 2025/0248950 | A1 | 8/2025 | Guy et al. |

FOREIGN PATENT DOCUMENTS

| | | | | | |
|---|---|---|---|---|---|
| CN | 101040855 | A | | 9/2007 | |
| CN | 103110582 | A | | 5/2013 | |
| CN | 104490873 | A | | 4/2015 | |
| CN | 108 236 608 | A | | 7/2018 | |
| CN | 109985042 | | * | 7/2019 | ............... A23L 2/02 |
| CN | 110 215 443 | A | | 9/2019 | |
| CN | 110 279 617 | A | | 9/2019 | |
| DE | 10 2012 105 063 | A1 | | 12/2013 | |
| EP | 2 311 475 | A2 | | 4/2011 | |
| EP | 2 448 637 | B1 | | 5/2012 | |
| EP | 2 578 561 | A1 | | 4/2013 | |
| EP | 2868319 | A1 | | 5/2015 | |
| EP | 3 157 512 | B1 | | 5/2018 | |
| GB | 2002754 | A | | 2/1979 | |
| GB | 2 377 633 | A | | 1/2003 | |
| GB | 2 380 129 | A | | 4/2003 | |
| GB | 2 381 194 | A | | 4/2003 | |
| GB | 2384707 | A | | 8/2003 | |
| GB | 2434097 | A | | 7/2007 | |
| GB | 2434312 | A | | 7/2007 | |
| GB | 2450753 | A | | 1/2009 | |
| GB | 2456183 | A | | 7/2009 | |
| GB | 2471523 | A | | 1/2011 | |
| GB | 2478595 | A | | 9/2011 | |
| GB | 2479153 | A | | 10/2011 | |
| GB | 2 485 291 | A | | 5/2012 | |
| GB | 2 487 183 | A | | 7/2012 | |
| GB | 2471565 | B | | 7/2012 | |
| GB | 2478072 | B | | 12/2012 | |
| GB | 2478074 | B | | 12/2012 | |
| GB | 2492487 | A | | 1/2013 | |
| GB | 2487712 | A | | 10/2015 | |
| GB | 2 530 001 | A | | 3/2016 | |
| GB | 2531093 | A | | 4/2016 | |
| GB | 2531278 | A | | 4/2016 | |
| GB | 2531281 | A | | 4/2016 | |
| GB | 2531282 | | * | 4/2016 | |

(56) References Cited

FOREIGN PATENT DOCUMENTS

| | | | | |
|---|---|---|---|---|
| GB | 2531282 A | * | 4/2016 | ............. A61P 43/00 |
| GB | 2539472 A | | 12/2016 | |
| GB | 2 542 155 A | | 3/2017 | |
| GB | 2438682 A | | 12/2017 | |
| GB | 2551987 A | | 1/2018 | |
| GB | 2584 140 A | | 11/2020 | |
| WO | WO-1999053917 A1 | | 10/1999 | |
| WO | WO 01/95899 A2 | | 12/2001 | |
| WO | WO 2002/064109 A2 | | 8/2002 | |
| WO | WO 02/089945 A2 | | 11/2002 | |
| WO | WO 2003/099302 A1 | | 12/2003 | |
| WO | WO 2004/016246 A1 | | 2/2004 | |
| WO | WO 2004/016277 A2 | | 2/2004 | |
| WO | WO 2004/026802 A1 | | 4/2004 | |
| WO | WO 2005/120478 A1 | | 12/2005 | |
| WO | WO 2006/054057 A2 | | 5/2006 | |
| WO | WO 2006/017892 A1 | | 12/2006 | |
| WO | WO 2006/133941 A2 | | 12/2006 | |
| WO | WO 2007/032962 A2 | | 3/2007 | |
| WO | WO 2007/052013 A1 | | 5/2007 | |
| WO | WO 2007/083098 A1 | | 7/2007 | |
| WO | WO 2007/138322 A1 | | 12/2007 | |
| WO | WO 2008/019146 A2 | | 2/2008 | |
| WO | WO-2008079295 A1 | | 7/2008 | |
| WO | WO 2008/094181 A3 | | 8/2008 | |
| WO | WO 2008/129258 A1 | | 10/2008 | |
| WO | WO-2008120207 A2 | | 10/2008 | |
| WO | WO 2008/144475 A1 | | 11/2008 | |
| WO | WO 2008/021394 A2 | | 12/2008 | |
| WO | WO 2008/146006 A1 | | 12/2008 | |
| WO | WO 2009/007697 A1 | | 1/2009 | |
| WO | WO 2009/007698 A1 | | 1/2009 | |
| WO | WO 2009/020666 A1 | | 2/2009 | |
| WO | WO 2009/093018 A1 | | 7/2009 | |
| WO | WO 2010/012506 A1 | | 2/2010 | |
| WO | WO 2011/001169 A1 | | 1/2011 | |
| WO | WO 2011/121351 A1 | | 10/2011 | |
| WO | WO 2012/033478 A1 | | 3/2012 | |
| WO | WO-2012071389 A2 | | 5/2012 | |
| WO | WO 2012/093255 A1 | | 7/2012 | |
| WO | WO 2012/160358 A1 | | 11/2012 | |
| WO | WO 2013/032351 A1 | | 3/2013 | |
| WO | WO 2013/045891 A1 | | 4/2013 | |
| WO | WO 2014/168131 A1 | | 11/2013 | |
| WO | WO-2014026802 A1 | | 2/2014 | |
| WO | WO 2014/108899 A1 | | 7/2014 | |
| WO | WO 2014/146699 A1 | | 9/2014 | |
| WO | WO 2015/065544 A1 | | 5/2015 | |
| WO | WO 2015/142501 A1 | | 9/2015 | |
| WO | WO 2015/184127 A2 | | 12/2015 | |
| WO | WO 2015/193667 A1 | | 12/2015 | |
| WO | WO 2015/193668 A1 | | 12/2015 | |
| WO | WO 2016/059399 A1 | | 4/2016 | |
| WO | WO 2016/059403 A1 | | 4/2016 | |
| WO | WO 2016/059405 A1 | | 4/2016 | |
| WO | WO 2016/084075 A1 | | 6/2016 | |
| WO | WO 2015/187988 A1 | | 7/2016 | |
| WO | WO 2016/118391 A1 | | 7/2016 | |
| WO | WO 2016/147186 A1 | | 9/2016 | |
| WO | WO 2016/022936 A1 | | 11/2016 | |
| WO | WO 2016/176279 A1 | | 11/2016 | |
| WO | WO 2016/191651 A1 | | 12/2016 | |
| WO | WO 2016/199148 A1 | | 12/2016 | |
| WO | WO 2016/203239 A1 | | 12/2016 | |
| WO | WO 2017/042567 A1 | | 3/2017 | |
| WO | WO 2017/139496 A1 | | 8/2017 | |
| WO | WO 2017/168138 A1 | | 10/2017 | |
| WO | WO 2017/203529 A1 | | 11/2017 | |
| WO | WO 2017/204986 A1 | | 11/2017 | |
| WO | WO 2018/002636 A1 | | 1/2018 | |
| WO | WO 2018/002637 A1 | | 1/2018 | |
| WO | WO 2018/002665 A1 | | 1/2018 | |
| WO | WO 2018/011808 A1 | | 1/2018 | |
| WO | WO 2018/037203 A1 | | 3/2018 | |
| WO | WO 2018/115962 A1 | | 6/2018 | |
| WO | WO 2018/200024 A1 | | 11/2018 | |
| WO | WO 2018/234811 A1 | | 12/2018 | |
| WO | WO 2019/020738 A1 | | 1/2019 | |
| WO | WO 2019/097238 A1 | | 5/2019 | |
| WO | WO 2019/145700 A1 | | 8/2019 | |
| WO | WO-2019178360 A1 | | 9/2019 | |
| WO | WO 2019/207319 A1 | | 10/2019 | |
| WO | WO 2019/210210 A1 | | 10/2019 | |
| WO | WO 2019/211795 A1 | | 11/2019 | |
| WO | WO 2020/225540 A1 | | 11/2020 | |
| WO | WO 2020/234569 A1 | | 11/2020 | |
| WO | WO 2021/019231 A1 | | 2/2021 | |
| WO | WO-2021255446 A1 | | 12/2021 | |

OTHER PUBLICATIONS

Akiyama, M. et al., “Dravet Syndrome:A Genetic Epileptic Disorder,” Acta. Med. Okayama, 66(5):369-376 (2012).

[Anonymous], “GW Pharma—GW Pharmaceuticals Announces New Physician Reports of Epidiolex® Treatment Effect in Children and Young Adults With Treatment-Resistant Epilepsy,” Oct. 14, 2014; https://ir.gwpharm.com/news-releases/news-release-details/gw-pharmaceuticals-announces-new-physician-reports-epidiolexr-0, 4 pages.

[Anonymous], “GW Pharmaceuticals Announces Epidiolex Receives Fast Track Designation from FDA for the Treatment of Dravet Syndrome,” GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.

[Anonymous], “Salutaris Drops Buy Salutaris Drops—Salutaris Drops,” Oct. 12, 2014; http://web.archive.org/web/20141012130255/http://salutarisdrops.com/buy-salutaris-drops/, 2 pages.

[Anonymous], “GW Pharmaceuticals Receives Orphan Drug Designation by FDA for Epidiolex® in the Treatment of Lennox-Gastaut Syndrome,” GW Pharmaceuticals Press Release, Feb. 28, 2014; https://www.gwpharm.com/ir/press-releases/gw-pharmaceuticals-receives-orphan-drug-designation-fda-epidiolexr-treatment, 4 pages.

[Anonymous], “Salutaris Drops Cannabidiol for Aicardi Syndrome—Salutaris Drops,” Oct. 12, 2014; http://web.archive.org/web/20141012220050/http://salutarisdrops.com/cannabidiol-aicardi-syndrome/, 3 pages.

[Anonymous], “GW Pharma Initiates Second Phase 3 Pivotal Study of Epidiolex® (CBD) in Lennox-Gastaut Syndrome,” Jun. 11, 2015; https://www.benzinga.com/pressreleases/18/11/g12748407/gw-pharmaceuticals-announces-second-positive-phase-3-pivotal-trial-for, 5 pages.

Approval Letter for NDA 210365 Epidiolex, Jun. 25, 2018, 12 pages.

Arzimanoglou et al., “All children who experience epileptic falls do not necessarily have Lennox-Gastaut syndrome . . . but many do,” Epileptic Disord. 2011, 13: S3-S13 (2011).

Booth, “Legalization’s opening of medical pot research is dream and nightmare,” Denver Post, Dec. 14, 2013, http://www.denverpost.com/ci_24726291/legalizations-opening-medical-pot-research-is-dream-and, 6 pages.

[No Author Listed], “ILAE Proposal for Revised Terminology for Organization of Seizures and Epilepsies,” 2010, 2 pages.

[No Author Listed] “Orphan Drug Designation Granted for Epidiolex in Dravet syndrome by the FDA-Seven Expanded Access INDs granted by FDA to US physicians to treat with Epidiolex 125 children suffering from intractable epilepsy syndromes,” GW Pharmaceuticals Press Release dated Nov. 14, 2013, 3 pages.

[No Author Listed] GW Pharmaceuticals Provides Update on Orphan Program in Childhood Epilepsy for Epidiolex, GW. Pharm. Available online Nov. 14, 2013, Retrieved Feb. 10, 2017, 5 pages.

[No Author Listed] “What are the Highest CBD Strains?” accessed Feb. 16, 2017, published Oct. 15, 2014, 2 pages.

[No Author Listed] “Cannabidiol Therapy for Aicardi Syndrome” Aug. 2014, 4 pages.

[No Author Listed] “Convulsive Disorders and Their Interference with Driving,” Medicos., Retrieved Feb. 10, 2017, Retrieved from

(56) References Cited

OTHER PUBLICATIONS internet: URL https://www.medicosporlaseguridadvial.com/en/clinical-subjects/neurologic-diseases/convulsive-disorders-and-their-interference-with-driving/, 2014, 3 pages.
[No Author Listed] "Estimating the Maximum Safe Starting Dose in Initial Clinical Trials for Therapeutics in Adult Healthy Volunteers," FDA Guidance for Industry, Jul. 2005, 30 pages.
[No Author Listed] "GW Pharmaceuticals Announces Physician Reports of Epidiolex Treatment Effect in Children and Young Adults with Treatment-resistant epilepsy from Physician-Led Expanded Access Treatment Program," GW Pharmaceuticals Press Release dated Jun. 17, 2014, 2 pages.
[No Author Listed], Cover and Table of Contents, J Pharmacology and Exp Therapeutics, Feb. 2010, 332(2), 4 pages.
[No Author Listed], "Missouri House passes cannabis extract legislation," Kansas City Star, 2014, https://kansascity.com/news/politics-government/article346747.html, 2 pages.
[No Author Listed], "High Rollers Bet on Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.
[No Author Listed], "Selected Media Examples of Pediatric Applications OfCannabidiol (CBD)," Jun. 30, 2013, 4 pages; https://www.420magazine.com/community/threads/selected-media-examples-of-pediatric-applications-of-cannabidiol-cbd.192155/.
[No Author Listed], "Medical Marijuana for N.J. Children? It's All in Gov. Christie's Hands," CBS News New York, Jun. 27, 2013, 3 pages; https://www.cbsnews.com/newyork/news/medical-marijuana-for-n-j-children-its-all-in-gov-christies-hands/.
Alger, B. E., "Not too excited? Thank your endocannabinoids," Neuron, 51(4):393-595 (2006).
Allen G., "Florida Bill Would Allow Medical Marijuana for Child Seizures," Jan. 16, 2014, retrieved from https://www.npr.org/sections/health-shots/2014/01/16/262481852/florida-bill-would-allow-marijuana-extract-for-child-seizures, 16 pages.
Amada, N. et al., "Cannabidivarin (CBDV) suppresses pentylenetetrazole (PTZ)-induced increases in epilepsy-related gene expression," 2013, PeerJ, 1: e214; 18 pages; http://dx.doi.org/10.7717/peerj.214.
American Epilepsy Society, Three Studies Shed New Light on the Effectiveness of Cannabis in Epilepsy, Oct. 14, 2014, 2 pages.
Ames, F. R. et al., "Anticonvulsant effect of cannabidiol," S Afr Med J. Jan. 4, 1986; 69(1):14, 1 page.
AAN 67th Annual Meeting Abstract, Apr. 2015; https://www.aan.com/PressRoom/Home/GetDigitalAsset/11570, 1 page.
Arain, A. M., "Pregabalin in the management of partial epilepsy," Neuropsychiatr Dis Treat., 407-13 (2009); Epub Aug. 20, 2009.
Arslan, A. & Tirnaksiz, F., "Self-emulsifying Drug Delivery Systems," F Abad J Pharm Sci, 38(1):55-64 (2013).
Avoli, M. et al., "Cellular and molecular mechanisms of epilepsy in the human brain," Prog Neurobiol., 77(3):166-200 (2005).
Babayeva et al., "Marijuana Compounds: A Non-Conventional Therapeutic Approach to Epilepsy in Children," J. Addict. Neuropharmacol, 1:1 (2014); doi:10.24966/AAD-7276/100002, 9 pages.
Bakhsh, K., "Pregabalin in the management of partial epilepsy," Miftaah-al-Khazaain, 1930:607-608, with English translation, 4 pages.
Bancaud, et al., "Proposal for Revised Clinical and Electroencephalographic Classification of Epileptic Seizures," Epilepsia, 22(4):489-501 (1981).
Banerjee et al., "Case Report: Aicardi syndrome: A report of five Indian cases," Neurology India, 54(1):91-93 (2006).
Barker-Haliski, M. et al., "How Clinical Development Can, and Should Inform Translational Science," Neuron, 84:582-593 (2014).
Bell, J., "Treatment With CBD in Oily Solution of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.
Benowitz, N. L. et al., "Metabolic and Psychophysiologic studies of cannabidiol hexobarbital interaction," Clin Pharmacol Ther., 28(1):115-120 (1980).
Benowitz & Jones, "Cardiovascular and metabolic considerations in prolonged cannabinoid administration in man," J Clin Pharm, 21:214S-223S, 1981.
Bergamaschi, M. M. et al., "Safety and Side Effects of Cannabidiol, a Cannabis sativa Constituent," Current Drug Safety, 6:237-249 (2011).
Bertram, E., "The Relevance of Kindling for Human Epilepsy," Epilepsia, 48(Suppl. 2):65-74 (2007).
Bipolar Health Group (Charlotte's Web Hemp Remedy, available online at http:/bipolarhealthgroup.org/index.php/charlottes-web-hemp-remedy/, accessed Sep. 6, 2017, 6 pages.
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, S. et al., "Modulation of mediotemporal and ventrostriatal function in humans by Delta9-tetrahydrocannabinol: a neural basis for the effects of Cannabis sativa on learning and psychosis," Arch Gen Psychiatry, 66(4): 442-451 (2009); doi:10.1001/archgenpsychiatry.2009 .17.
Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.
Bostanci, M. O. & Bagirici, F., "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brown et al., Child Neurology Foundation, "LGS" (Lennox-Gastaut Syndrome), available at http://www.childneurologyfoundation.org/disorders/lgs-lennox-gastaut-syndrome, 2019, 7 pages.
ChildNeurologyFoundation.org [online], "Disorder Directory: Learn from the Experts—LGS (Lennon-Gastaut Syndrome)," Child Neurology Foundation, available on or before Sep. 6, 2015, retrieved on May 21, 2018; URL http://www.childneurologyfoundation.org/disorders/lgs-Lennox-gastaut-syndrome, 10 pages.
Brust, J. C. M. et al., "Marijuana use and the risk of new onset seizures," Trans Am Clin Climatol Assoc., 103:176-181 (1992).
"Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.
Camfield, "Definition and natural history of Lennox-Gastaut Syndrome," Epilepsia, 52:3-9 (2011).
Campos-Castello, "Rational approach to treatment options for Lennox-Gastaut syndrome," Orphanet, Mar. 2003; https://www.orpha.net/data/patho/GB/uk-Lennox.pdf, 5 pages.
Capal, J. K. & Franz, D. N., "Profile of everolimus in the treatment of tuberous sclerosis complex: an evidence-based review of its place in therapy," Neuropsychiatric Disease and Treatment, 12:2165-2172 (2016).
Carlini, et al., "Hypnotic and antiepileptic effects of cannabidiol," J Clin Pharmacol. Aug.-Sep. 21, 1981;(8-9 Suppl):417S-427S. Medline abstract only.
Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158. 1973.tb10660.x.
Carvill, G. L. et al., "GABRA1 and STXBP1: Novel generic causes of Dravet Syndrome," Neurology, 82:1245-1253 (2014).
Castel-Branco, et al., "The Maximal Electroshock Seizure (MES) Model in the Preclinical 98. Assessment of Potential New Anti epileptic Drugs," Methods Find Exp Clin Pharmacol., 31(2): 101-106 (2009).
cdc.gov [online], "2 to 20 years: Girls Stature-for-age and Weight-for-age percentiles," National Center for Health Statistics and National Center for Chronic Disease Prevention and Health Promotion, last modified Nov. 2000, https://www.cdc.gov/growthcharts/data/set1clinical/cj411022.pdf, 1 page.

(56) References Cited

OTHER PUBLICATIONS

Charlotte's Web [ online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
Chiron, C. & Dulac, O., "The Pharmacologic Treatment of Dravet Syndrome," Epilepsia, 52 (Suppl. 2):72-75 (2011).
Chiron, S., "Stiripentol for the treatment of Dravet syndrome," Orphan Drugs: Research and Reviews, 4:29-38 (2014).
Chiu, P. et al., "The Influence of Cannabidiol and A-Tetrahydro-cannabinol on Cobalt Epilepsy in Rats," Epilepsia, 20:365-375 (1979).
Chou, "Theoretical basis, experimental design, and computerized simulation of synergism and antagonism in drug combination studies," Pharmacol Rev, 58(3):621-681 (2006).
Christians, U. et al., "Biomarkers of Immunosuppressant Organ Toxicity after Transplantation—Status, Concepts and Misconceptions," Expert Opin Drug Metab Toxicol., 7(2): 175-200 (2011).
Chu-Shore, C. J. et al., "The natural history of epilepsy in tuberous sclerosis complex," Epilepsia, 51(7):1236-1241, 2010; doi: 10.1111/j.1528-1167.2009.02474.
Ciccone, "Drop Seizure Frequency in Lennox-Gastaut Decrease With Cannabidiol," Neurology Advisor, Apr. 26, 2017; retrieved from the Internet: URL: https://neurologyadvisor.com/aan-2017-coverage/aan-2017-cannabidiol-reduces-drop-seizures-in-lennox-gasaut-syndrome/article/652931, 6 pages.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online. <http://faces.med.nyu.edu/research-education/cannabidiol-conference>, 44 pages.
Cilio, M. R. et al., "The case for assessing cannabidiol I epilepsy," Epilepsia, 55(6):787-790 (2014).
Citti et al., "Pharmaceutical and biomedical analysis of cannabinoids: A critical review," Journal of Biopharmaceutical and Biomedical Analysis, 147:565-579 (2018).
Clinical Trials.Gov [online], Identifier: NCT02224690, A Study to Investigate the Efficacy and Safety of Cannabidiol (GWP42003-P; CBD) as Adjunctive Treatment for Seizures Associated With Lennox-Gastaut Syndrome in Children and Adults (GWPCARE4), Jazz Pharmaceuticals, U.S. National Library of Medicine, last update posted Sep. 8, 2022, 3 pages; Retrieved from https://clinicaltrials.gov/ct2/show/NCT02224690.
Clinical Trials.Gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.
Clinical Trials.Gov [online], Identifier: NCT02006628, A study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
Clinical Trials.Gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
Clinical Trials.Gov [online], Identifier: NCT02544750, "An open-label Extension Trial of Cannabidiol (GWP42003-P, CBD) for Seizures in Tuberous Sclerosis Complex (GWPCARE6)," Sponsor: GW Research Ltd, U.S. National Library of Medicine, Oct. 1, 2018; Retrieved from https://clinicaltrials.gov/ct2/show/NCT02544750, 6 pages.
Clinical Drug Interaction Studies—Cytochrome P450 Enzyme- and Transporter-Mediated Drug Interactions Guidance for Industry, U.S. Department of Health and Human Services, Food and Drug Administration, Center for Drug Evaluation and Research (CDER), Jan. 2020, 27 pages.
Collins, T. R., Collins TR. What Neurologists are Doing About Medical Marijuana?, Neurology Today, Apr. 17, 2014, vol. 4, issue 8, 8 pages.
Conry, J. A. et al., "Clobazam in the treatment of Lennox-Gastaut syndrome," Epilepsia, 50:1158-1166 (2009).
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marihuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Controlled clinical trial of cannabidiol in Huntington's Disease," Pharmacology Biochemistry & Behavior, 40:701-708 (1991).
Consroe, et al., "Effects of cannabidiol on behavioral seizures caused by convulsant drugs or current in mice," Eur J Pharmacol., 83(3-4):293-298 (1982).
Consroe et al., "Chapter 2: Therapeutic Potential of Cannabinoids in Neurological Disorders," Cannabonioids as Therapeutic Agents, R. Mechoulam, Ed., 1986, pp. 21-49.
Consroe, et al. Chapter 12, "Potential Role of Cannabinoids for Therapy of Neurological Disorders." p. 459 in Marijuana Cannabinoids: Neurobiology and Neurophysiology, ed. L. Murphy (1992), 72 pages.
Consroe et al., "Open label evaluation of cannabidiol in dystonic movement disorders," International Journal of Neuroscience, 30(4):277-282 (1986); doi: 10.3109/00207458608985678.
Cortesi, et al., "Potential therapeutical effects of cannabidiol in children with pharmacoresistant epilepsy," Med Hypotheses, 68(4):920-921 2007). Epub Nov. 16, 2006.
Cortez, et al. Chapter 10, "Pharmacologic Models of Generalized Absence Seizures in Rodents," Models of Seizures and Epilepsy, 111-126 (2006).
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Crespel, A. et al., "Lennox-Gastaut Syndrome," Chapter 14, in Epileptic Syndromes in Infancy, Childhood, and Adolescence, 5th Edition, ed. M. Bureau, et al., pp. 189-216.
Crumrine, P. K., "Management of Seizures in Lennox-Gastaut Syndrome," Pediatr Drugs, 13(2):107-118 (2011).
Cunha, et al., "Chronic administration of cannabidiol to healthy volunteers and epileptic patients," Pharmacology, 21(3):175-85 (1980).
Curatolo, P. et al., "Management of epilepsy associated with tuberous sclerosis complex (TSC): Clinical recommendations," European Journal of Paediatric Neurology, 16:582-586 (2012).
Curia et al., "The pilocarpine model of temporal lobe epilepsy," J Neuroscience Methods, 172(2-4):143-157 (2008).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150:S162 (1997), 2 pages.
Dasa, et al. "Brhat Nighantu Ratnakara (Saligramanighantubhusanam)." vol. IV. 1997:170. Sanskrit. Exhibit 5, 5 pages.
Davis, et al., "A predominant role for inhibition of the adenylate cyclase/protein kinase. A pathway in ERK activation by can-

(56) References Cited

OTHER PUBLICATIONS nabinoid receptor 1 in NIE-115 neuroblastoma cells," J Biol Chem., 278(49):48973-80 (2003). Epub Sep. 29, 2003.
Davis, et al., "Antiepileptic action of marijuana-active substances," Federation Proceedings, 8:284-5 (1949).
Depakene (valproic acid) capsules and oral solution, CV, Prescribing Information, 1978, 54 pages; https://www.accessdata.fda.gov/drugsatfda_docs/label/2013/018081s056lbl.pdf.
Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.
De Oliveira, et al., "Anticonvulsant activity of β-caryophyllene against pentylenetetrazol-induced seizures," Epilepsy Behav., 56:26-31 (2016); doi: 10.1016/j.yebeh.2015.12.040.
De Meijer, "The Chemical Phenotypes (Chemotypes) of Cannabis," Chapter 5, Handbook of Cannabis, ed. Roger G. Pertwee, pp. 89-110 (2014).
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>, 16 pages.
Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-Epilepsy AAN-POSTER Apr. 8, 2015.pdf, 1 page.
Devinsky, et al., "Cannabidiol: Pharmacology and potential therapeutic role in epilepsy and other neuropsychiatric disorders," Epilepsia, 55(6):791-802 (2014).
Devinsky et al., "Efficacy and safety of Epidiolex (cannabidiol) in children and young adults with treatment-resistant epilepsy: Initial data from expanded access program," Jan. 2015, 2 pages.
Devinsky et al., "Cannabidiol in patients with treatment-resistant epilepsy: an open-label interventional trial," Lancet Neurology, 15(3):270-278 (2015).
Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017), 2 pages.
Devinsky et al., "Trial of Cannabidiol for Drug-Resistant Seizures in the Dravet Syndrome," N Engl J Med, 376(21):2011-2020 (2017).
Diacomitt Product Monograph, Submission Control 142417, Date of Preparation, Dec. 19, 2012, 37 pages.
Dilantin-125®, NDA 08762 Dilantin-125 (Phenytoin Oral Suspension, USP) FDA Approved Labeling Text dated Feb. 2013, 15 pages.
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online. <http://faces.med.nyu.edu/research-education/cannabidiol-conference>, 32 pages.
Dimarzo, V., Declaration Under 37 C.F.R. 1.132, dated Aug. 24, 2017, 21 pages.
Dravet, "The core Dravet syndrome phenotype," Epilepsia, 52 Suppl 2:3-9 (2011); doi: 10.1111/j.1528-1167.2011.02994. x.
Dreifus, et al., "Proposal for Revised Clinical and Electroencephalographic Classification of Epileptic Seizures," Epilepsie., 22:489-501 (1981).
Drugs of the Future, 39(1): 49-56, Jan. 2014 notes Orphan Drug designation for CBD for Lennox-Gastaut Syndrome.
Dulac, "Use of Lamotrigine in Lennox-Gastaut and Related Epilepsy Syndromes," J. Child Neurolog., 12(Supplement 1): S23-S29 (1997).
Dulac, "Vigabatrin in Childhood Epilepsy," J. Child Neurolog., 6(Supplement 2): S30-S37 (1991).
Eadie, "Shortcomings in the current treatment of epilepsy," Expert Rev Neurother., 12(12):1419-27 (2012).
Ebrahimi-Fakhari, D. et al., "Cannabidiol Elevates mTOR Inhibitor Levels In Tuberous Sclerosis Complex Patients," (2020) Pediatric Neurology, 12 pages; https://doi.org/10.1016/j.pediatrneurol.2019.11.017.
Engel, "Report of the ILAE classification core group," Epilepsia, 47(9):1558-68 (2006).
Engel, "What should be modeled," in Models Seizure Epilepsy, 2006, 14 pages.
Eggers, "Temporal lobe epilepsy is a disease of faulty neuronal resonators rather than oscillators, and all seizures are provoked, usually by stress," Med Hypotheses.,69(6):1284-9 (2007).
Epilepsy Patients Flock to Colorado after Medical Pot Gives Them Hope, Nov. 18, 2013, CBS Colorado News, 4 pages.
Elsohly and Gul, "Constituents of Cannabis Sariva," Chapter 1, Handbook of Cannabis, Roger G. Pertwee, Ed., pp. 3-22 (2014).
Elsohly, M. & Gul, W., "Chemical constituents of marijuana: The complex mixture of natural cannabinoids," Life Sciences, 78:539-548 (2005).
Epidiolex® (cannabidiol) oral solution, CV, Prescribing Information, 2018, 30 pages; https://www.accessdata.fda.gov/drugsatfda_docs/label/2018/210365lbl.pdf.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
FDA'S Guidance for Industry Q3A Impurities in New Drug Substances, Revision 2, Jun. 2008, 17 pages.
FDA Guideline for Submitting Supporting Documentation in Drug Applications for the Manufacture of Drug Substances, published in 1987, 20 pages.
Fariello, "Parenteral Penicillin in Rats: An Experimental Model of Multifocal Epilepsy," Epilepsia, 17:217-222 (1976).
Ferdinand, et al., "Cannabis-psychosis pathway independent of other types of psychopathology," Schizophr Res., 79(2-3):289-295 (2005).
Fernandez-Ruiz, J. et al., "Cannabidiol for neurodegenerative disorders: important new clinical applications for this phytocannabinoid?" British Journal of Pharmacology, 75(2):323-333 (2012).
Fisher, et al., "The impact of epilepsy from the patient's perspective I. Descriptions and subjective perceptions," Epilepsy Res.,41(1):39-51 (2000).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online. <http://faces.med.nyu.edu/research-education/cannabidiol-conference>, 22 pages.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online. <http://faces.med.nyu.edu/research-education/cannabidiol- conference>, 14 pages.
Gabor, et al., "Lorazepam versus phenobarbital: Candidates for drug of choice for treatment of status epilepticus," J Epilepsy, 3(1):3-6 (1990).
Gallily, et al., "Overcoming the Bell-Shaped Dose-Response of Cannabidiol by Using Cannabis Extract Enriched in Cannabidiol," Pharmacology & Pharmacy, 6:75-85 (2015).
Gaoni, Y. & Mechoulam, R., "The Isolation and Structure of Δ1-Tetrahydrocannabinol and Other Neutral Cannabinoids from Hashish," J Am Chem Soc. Jan. 13, 1971;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "Gw Pharmaceuticals Announces Physician Reports of Epidiolex Treatment Effect in Children and Young Adults With

(56) References Cited

OTHER PUBLICATIONS

Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Gastaut, "Clinical and electroencephalographical classification of epileptic seizures," Epilepsia, 10:Suppl:2-13 (1969).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gedde, Retrospective Case Review of High CBD, Low THC Cannabis Extract (Realm Oil) for Intractable Seizure Disorders, 2013 Realm of Caring Foundation, 4 pages.
Gedde, "Clinical Experience with Cannabis in Treatment-Resistant Pediatric Epilepsy," http://www.theroc.us/images/gedde presentation.pdf, Sep. 9-11, 2014, 45 pages.
Gedde et al., "3.330 Whole Cannabis Extract of High Concentration Cannaboidol May Calm Seizures in Highly Refractory Pediatric Epilepsies," American Epilepsy Society, Dec. 2013, pp. 449-1450.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Geffrey et al., "Drug-drug interaction between clobazam and cannabidiol in children with refractory epilepsy," Epilepsia, 56(8):1246-1251 (2015).
Gillen, D., "How Does Caffeine Affect CBD?", Apr. 21, 2019, available at: https://web.archive.org/web/20191220210719/https://greendoorcbd.com/blogs/news/how-does-caffeine-affect-cbd, 4 pages.
Gloss, D. & Vickrey, B., "Cannabinoids for epilepsy (Review)," Cochrane Database of Systematic Reviews 2014, Issue 3. Art. No. CD009270, 9 pages; DOI: 10.1002/14651858.CD009270.pub3.
Green, "CBD: An Unconventional Therapy," available online at http://nugs.com/article/cbd-anunconventional-therapy.html, published Mar. 24, 2014, 5 pages.
Green Roads CBD Coffee and Tea, Product Page, 2023, 5 pages; https://greenroads.com/collections/cbd-tea-cbd-coffee?nfsn=2488702.aa938d.
Gresham, et al., "Treating Lennox-Gastaut syndrome in epileptic pediatric patients with third generation rufinamide," Neuropsychiatr Dis Treat., 6:639-645 (2010).
Gross, et al., "Marijuana use and epilepsy: prevalence in patients of a tertiary care epilepsy center," Neurology, 62(11):2095-7 (2004).
Grotenhermen et al., "The Therapeutic Potential of Cannabis and Cannabinoids," Dtsch Arztebl Int, 109(29-30): 495-501 (2012); doi:10.3238/arztebl.2012.0495.
Guerrini, et al., "Lamotrigine and Seizure Aggravation in Severe Myoclonic Epilepsy," Epilepsia, 39(5):508-512 (1998).
Guimares, et al., "Antianxiety effect of cannabidiol in the elevated plus-maze," Psychopharmacology (Berl)., 100(4):558-9 (1990); doi: 10.1007/BF02244012.
Goodman & Gilman, The Pharmacological Basis of Therapeutics (Brunton, Laurence L.; Lazo, John S.; Parker, Keith, eds. (2006); New York: McGraw-Hill. ISBN 0-07-142280-3); Chapter 19, Pharmacotherapy of the Epilepsies, 28 pages.
Gupta Video 2013, Weed—CNN Special; https://www.youtube.com/watch?v=Z3IMfl1_K6U.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, 8 pages.
GWPharm [online], "GW Pharmaceuticals Provides Update on Orphan Program in Childhood Epilepsy for Epidiolex®," GW Pharmaceuticals Press Release, Nov. 15, 2013, 5 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, 5 pages.
GWPharm [online], "GW Pharmaceuticals Announces Preliminary Results of Phase 2a Study for its Pipeline Compound GWP42006," Gw Pharmaceuticals Press Release, Feb. 21, 2018, 5 pages.
Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.
Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.
Hauser, N. et al., "High on Cannabis and Calcineurin Inhibitors: A Word of Warning in an Era of Legalized Marijuana," Hindawi Publishing Corporation, Case Reports In Transplantation, vol. 2016, Sep. 6, 2018;2018:7095846. doi: 10.1155/2018/7095846. eCollection 2018, 4 pages.
Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J_tot_lament_medical_marijuana_delays.html.
Hegde, M. et al., "Seizure exacerbation in two patients with focal epilepsy following marijuana cessation," Epilepsy & Behavior, 25:563-566 (2012).
Heinemann, et al., "An Overview of in Vitro Seizure Models in Acute and Organotypic Slices," Chapter 4, 35-44 (2006).
Hess et al., "Cannabidiol as a new treatment for drug-resistant epilepsy in tuberous sclerosis complex," Epilepsia, 57(10): 1617-1624 (2016).
Hill, et al., "Δ9-Tetrahydrocannabivarin suppresses in vitro epileptiform and in vivo seizure activity in adult rats." Epilepsia, 51(8):1522-32 (2010); doi: 10.1111/j.1528-1167.2010.02523. x. Epub Feb. 26, 2010.
Hill, "Cannabidivarin-rich cannabis extracts are anticonvulsant in mouse and rat via a CB 1 receptor-independent mechanism," British Journal of Pharmacology, 170(3):679-692 (2013).
Hill et al., "Cannabidivarin is anticonvulsant in mouse and rat," Br. J Pharmacol, 167(8):1629-1642 (2012).
Hill, A. J. et al., "Phytocannabinoids as novel therapeutic agents in CNS disorders," Pharmacology & Therapeutics, 133:79-97 (2012).
Hillig, K. W. & Mahlberg, P. G., "A chemotaxonomic analysis of cannabinoid variation in Cannabis (Cannabaceae)," American Journal of Botany, 91(6):966-975 (2004).
Holmes, et al., "Choosing the correct AED: From Animal Studies to the Clinic," Pediatr Neurol. 38(3):151-162 (2008).
Holmes, G. L. et al., "Tuberous Sclerosis Complex and Epilepsy: Recent Developments and Future Challenges," Epilepsia, 48(4):617-630, 2007.
Iannotti, et al., "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-41 (2014); doi: 10.1021/cn5000524.
ICE Epilepsy Alliance, The Dravet Syndrome Spectrum, Nov. 2008, 2 pages.
IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.

(56) References Cited

OTHER PUBLICATIONS

Iuvone, et al., "Neuroprotective effect of cannabidiol, a non-psychoactive component from Cannabis sativa, on beta-amyloid-induced toxicity in PC12 cells," J Neurochem., 89(1 ):134-41 (2004).
Iwasaki, I., "Metabolism of Tacrolimus (FK506) and Recent Topics in Clinical Pharmacokinetics," Drug Metab. Pharmacokinet., 22(5):328-335 (2007).
Izzo, et al., "Non-psychotropic plant cannabinoids: new therapeutic opportunities from an ancient herb," Trends in Pharmacological Sciences, 30(10):515-527 (2009).
Jacobson, "Survey of Current Cannabidiol Use in Pediatric Treatment-Resistant Epilepsy," Apr. 22, 2013; https://www.thcint.com/uploads/1/9/3/7/19371199/cannabidiol_use_in_pediatric_epilepsy.pdf, 1 page.
Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with-pharmaceutical-grade-cbd/.
Jaeger, W. et al., "Inhibition of cyclosporine and tetrahydrocannabinol meabolism by cannabidiol in mouse and human microsomes," Xenobiotica, 26(3):275-284 (1996).
Jeavons, et al., "Sodium valproate in treatment of epilepsy," Br Med J., 2(5919):584-6 (1974).
Jiang, R. et al., "Cannabidiol Is a Potent Inhibitor of the Catalytic Activity of Cytochrome P450 2C19," Drug Metab. Pharmacokinet., 28(4):332-338 (2013).
Jones et al. [online], Info & Metrics / Article Information,"Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Jones et al., "Cannabidiol Displays Antiepileptiform and Antiseizure Properties in Vitro and in Vivo," J Pharmacol Exp Ther., 332(2):559-577 (2010).
Jones, N. A. et al., "Cannabidiol exerts anti-convulsant effects in animal models of temporal lobe and partial seizures," Seizure, 21:344-352 (2012).
Jones, P. G. et al., "Cannabidiol," Acta Cryst., B33:3211-3214 (1977).
Joy, et al., "Marijuana and Medicine. Assessing the Science Base," National Academy Press. Washington D.C., 1999, 170 pages.
Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013), 25 pages; Video published online. <http://faces.med.nyu.edu/research-education/cannabidiol-conference>.
Kahan, et al., "Risk of selection bias in randomized trials," Trials, 16:405 (2015), 7 pages.
Karler, et al., "The cannabinoids as potential antiepileptics," J Clin Pharmacol, 21(8-9 Suppl):437S-447S (1981).
Karler et al., "The anticonvulsant activity of cannabidiol and cannabinol," Life Science, 13:1527-1531 (1973).
Kalepu, S. et al., "Oral lipid-based drug delivery systems—an overview," Acta Pharmaceutica Sinica B., 3(6):361-372 (2013).
Kaplan, "F.D.A. Panel Recommends Approval of Cannabis-Based Drug for Epilepsy," NY Times, Apr. 19, 2018, retrieved on Jun. 20, 2018, URL <https://www .nytimes.com/2018/04/19/health/epidiolex-fda-cannabis-marajuana.html>, 3 pages.
Kassai et al., "Severe Myoclonic epilepsy in Infancy: A Systematic Review and a Meta-Analysis of Individual Patient Data," Epilepsia, 49(2):343-348 (2008).
Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online. <http://faces.med.nyu.edu/research-education/cannabidiol-conference>, 25 pages.
Kerr, D. N. S. & Pillai, P. M., "Clobazam as adjunctive treatment in refractory epilepsy," British Medical Journal, 286:1246-1247 (1983).
Khan et al., "Key Attributes of TKDL: Laooq-e-Quinnab/Barai Zeequn-Nafs," Khazaain-al-Advia, 1911 (with English translation), 2 pages.
Khan et al., Key Attributes of TKDL: Nushka-e-Qutoor, Muheet-e-Azam, 1887 (with English translation), 2 pages.
Khan et al., "Key Attributes of TKDL: Sufoof-e-Qinnab Barae Waja," Khazaain-al-Adiva, 1911, (with English translation), 5 pages.
Khan et al., "Key Attributes of TKDL: Usaara-e-Qinnab Barai Qoolanj," Khazaain-al-Advia, 1911 (with English translation), 6 pages.
Khan et al., "Key Attributes of TKDL: Zimad-e-Qinnab," Khazaain-al-Adiva, 1911 (with English translation), 5 pages.
Kelley, et al., "Doose syndrome (myoclonic-astatic epilepsy): 40 years of progress," Developmental Medicine & Child Neurology, 52:988-993 (2010).
Klitgaard, et al., "Electrophysiological, neurochemical and regional effects of levetiracetam in the rat pilocarpine model of temporal lobe epilepsy," Seizure, 12(2):92-100 (2003).
Klitgaard, et al., "Evidence for a unique profile of levetiracetam in rodent models of seizures and epilepsy," European Journal of Pharmacology, 353(2):191-206 (1998).
Kopka, M., "Cannabinoids in the treatment of epilepsy—an updated review," Journal of Epileptology, 2019, 27:35-42; 10.21307/jepil-2019-004.
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250.x. Epub Aug. 29, 2011.
Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.
Kruk-Slomka et al., "A comparison of mecamylamine and bupropion effects on memory-related responses induced by nicotine and scopolamine in the novel object recognition test in mice," Pharmacological Reports, 66(4):638-646 (2014).
Kuhn et al., "Potent activity of carfilzomib, a novel, irreversible inhibitor of the ubiquitin-proteasome pathway, against preclinical models of multiple myeloma," Blood, 110(9):3281-3290 (2007).
Kurz & Blass, "Use of dronabinol (delta-9-THC) in autism: A prospective single-case-study with an early infantile autistic child," Cannabinoids, 5(4):4-6 (2010).
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j.1528-1167.2009.02397. x. Epub Nov. 3, 2009. Erratum in: Epilepsia. Sep. 2010;51(9): 1922.
Laprarie et al., "Cannabidiol is a negative allosteric modulator of the cannabinoid CB1 receptor," British J Pharmacology, 172(20):4790-4805 (2015).
LeafScience.com [online], "What are the Highest CBD Strains?" Oct. 15, 2014, retrieved on Feb. 16, 2017, URL www.leafscience.com/2014/10/15/highest-cbd-strains/, 2 pages.
Leahy, J. T. et al., "Clobazam as an adjunctive therapy in treating seizures associated with Lennox-Gastaut syndrome," Neuropsychiatric Disease and Treatment, 7:673-681 (2011).
Leino, A. et al., "Evidence of a clinically significant drug-drug interaction between cannabidiol and tacrolimus: A case report," American Journal of Transplantation, 18 (Suppl. 4): 744-745 (2018).
Leo, et al., "Cannabidiol and epilepsy: Rationale and therapeutic potential," Pharmacological Research, 107:85-92 (2017).
Leo et al., "Antiepileptogenic effects of Ethosuximide and Levetiracetam in WAG/Rij rats are only temporary," Pharmacological Reports, 71:833-838 (2019).
Leo et al., "Cognitive impairment in the WAG/Rij rat absence model is secondary to absence seizures and depressive-like behavior," Progress in Neuropsychopharmacology & Biological Psychiatry, 94:109652 (2019), 16 pages.
Leonard, B. E., "Therapeutic Uses of Cannabis," British Medical Association (BMA). Harwood Academic Publishers, UK. 1997, p. 592.
Lewis, "Mystery Mechanisms," The Scientist.com, Jul. 29, 2016, retrieved on Nov. 8, 2017, 2 pages.

(56) References Cited

OTHER PUBLICATIONS

Lieu, et al., "Assessment of self-selection bias in a pediatric unilateral hearing loss study," Otolaryngol Head Neck Surg., 142(3):427-433 (2010).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-78 (2011); doi:10.1111/j.1528-1167.2011.03024. x.
Loscher, W. & Rogawski, M. A., "How theories evolved concerning the mechanism of action of barbiturates," Epilepsia, 53(Suppl. 8): 12-25, 2012; doi: 10.1111/epi.12025.
Lutz, "On-demand activation of the endocannabinoid system in the control of neuronal excitability and epileptiform seizures," Biochem Pharmacol., 68(9):1691-8 (2004).
Lowenstein, "Chapter 363: Seizures and Epilepsy," Diseases of the Central Nervous System, 2498-2512 (2008).
Luttjohann, et al., "A revised Racine's scale for PTZ-induced seizures in rats," Physiol Behav., 98(5):579-86 (2009); doi: 10.1016/j.physbeh.2009.09.005.
Maa et al., "The case for medical marijuana in epilepsy," Epilepsia, 55(6):783-786 (2014).
Marks, W. J. et al., "Management of Seizures and Epilepsy," Am Fam Physician. 1998;57(7):1589-1600.
Mackie, "Cannabinoid receptors as therapeutic targets," Annu Rev Pharmacol Toxicol., 46:101-22 (2006).
Majoosi, et al. Kaamil-al-Sena'ah, Part II, Central Council for Research in Unani Medicine. 2005: 116. Arabic. Exhibit 2, 2 pages.
Malamut, M., "I Drank CBD Coffee for a Week. Here's What I Did to My Anxiety," Nov. 18, 2019, available at https://www.healthline.com/health/mental-health/i-tried-it-cbd-coffee-anxiety, 16 pages.
Malfait, et al. "The nonpsychoactive cannabis constituent cannabidiol is an oral anti-arthritic therapeutic in murine collagen-induced arthritis," PNAS, 97(17):9561-9566 (2000).
Manni et al., "Obstructive Sleep Apnea in a Clinical Series of Adult Epilepsy Patients: Frequency and Features of the Comorbidity," Epilepsia, 44(6):836-840 (2003).
Marinol® Product Description, NDA 18-651/S-025 and S-026, Jul. 2006, pp. 3-13.
Manno, "Status Epilepticus: Current Treatment Strategies," The Neurohospitalist, 1(1):23-31 (2011).
Masangkay, E. G., "Fda Confirms GW Pharmaceuticals' IND for Epidiolex Trial in Dravet Syndrome," May 9, 2014, 2 pages; FDA Confirms GW Pharmaceuticals' IND For EpidiolexTrial in Dravet Syndrome.
Mattson, et al., "Comparison of carbamazepine, phenobarbital, phenytoin, and primidone in partial and secondarily generalized tonic-clonic seizures," N. Engl. J. Med, 313(3):145-151 (1985).
Mattson, et al., "Prognosis for total control of complex partial and secondary generalized tonic clonic seizures," Neurology, 47:68-76 (1996).
Mares et al., "Electrical Stimulation-Induced Models of Seizures in Model of Seizures and Epilepsy Asla Pitkanen," Philip A. Schwartzkroin & Solomon L. Moshe, eds., 2006, 7 pages.
Martin et al., "Structure-Anticonvulsant Activity Relationships of Cannabidiol Analogs," National Institute on Drug Abuse, Research Monograph Series, 79:48-58 (1987).
McCormick et al., "On the cellular and network bases of epileptic seizures," Annu Rev Physiol., 63:815-46 (2001).
McNamara, "Chapter 19: Pharmacotherapy of the Epilepsies,", Goodman & Gilman's The Pharmacological Basis of Therapeutics 11th ed., McGraw-Hill Companies, pp. 501-525 (2006).
Mechoulam, et al., "Cannabidiol: An Overview of Some Pharmacological Aspects," J Clin Pharmacol, 42:11S-19S (2002).
Mechoulam, et al., Toward drugs derived from cannabis, Naturwissenschaften, 65(4):174-9 (1978).
Mechoulam, R. et al., "Cannabidiol—Recent Advances," Chemistry & Biodiversity, vol. 4, pp. 1678-1692 (2007).
Mechoulam, R., "Conversation with Ralph Mechoulam," Addiction Jun. 2007; 102(6):887-93. doi: 10.1111/j.1360-0443.2007.01795. x . . . .
Mechoulam, R. & Parker, L. A., "The Endocannabinoid System and the Brain," Annu. Rev. Psychol. 2013. 64:21-47.
Mechoulam, R. & Parker, L. A., "Towards a better cannabis drug," British Journal of Pharmacology (2013) 170 1363-1364.
Mechoulam et al., "Cannabidiol: an overview of some chemical and pharmacological aspects. Part I: chemical aspects," Chemistry and Physics of Lipids, 121:35-43 (2002).
Merlis, "Proposal for an international classification of the epilepsies," Epilepsia, 1(1):114-9 (1970).
Miller, et al., "Mapping genetic modifiers of survival in a mouse model of Dravet syndrome," Genes, Brain and Behavior, 13:163-172 (2014).
Montenegro et al., "Efficacy of Clobazam as Add-on Therapy for Refractory Epilepsy: Experience at a US Epilepsy Center," Clinical Neuropharmacology, 31(6):333-338 (2008).
Montouris, "Rational approach to treatment options for Lennox-Gastaut syndrome," Epilepsia, 52:10-20 (2011).
Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
Morard, et al., "Conversion to Sirolimus-Based Immunosuppression in Maintenance Liver Transplantation Patients," Liver Transplantation, 13:658-664 (2007).
Moral, et al., "Pipeline on the Move," Drugs of the Future, 39(1):49-56 (2014).
Morelli et al., "The effects of cannabidiol and its synergism with bortezomib in multiple myeloma cell lines. A role for transient receptor potential Vanilloid type-2," Blood, 110(9):3281-3290 (2014).
MyVirtualMedicalCentre [online], "Aicardi syndrome," mymc.com, Feb. 2004, retrieved on Jan. 25, 2019 at https://www.myvmc.com/diseases/aicardi-syndrome/, 6 pages.
Nabissi et al., "Cannabinoids synergize with carfilzomib, reducing multiple myeloma cells viability and migration," Oncotarget, 7:77553 (2016), 15 pages.
Nair et al., "A simple practice guide for dose conversion between animals and human," Journal of Basic and Clinical Pharmacy, 7:27-31 (2016).
Ng et al., "Illicit drug use and the risk of new-onset seizures." Am J Epidemiol., 132(1):47-57 (1990).
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
New Drug Application No. 210365 for Epidiolex (cannabidiol) 100 mg/ml oral solution, Jun. 25, 2018, 12 pages.
[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWN0OL01D20140606.
[No Author Listed], "Medical Cannabis Community Wants to Remain Apart," Medical Marijuana News, Apr. 3, 2013, 3 pages; Kitsap Peninsula Business Journal, available at: https://www.420magazine.com/community/threads/medical-cannabis-community-wants-to-remain-apart. 186955/.
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
Onfi™ (clobazam) tablets Prescribing Information, NDA 202067 Onfi (clobazam) Tablets for oral use FDA Approved Labeling Text, dated Oct. 21, 2011, 28 pages.
Oguni, H. et al., "Long-Term Prognosis of Lennox-Gastaut Syndrome," Epilepsia, 37(Suppl 3):44-47 (1996).

(56) References Cited

OTHER PUBLICATIONS

Oguni, H. et al., "Severe myoclonic epilepsy in infants—a review based on the Tokyo women's Medical University series of 84 cases," Brain Dev., 23:736-748 (2010).
Olyaei, A. J. et al., "Interaction Between Tacrolimus and Nefazodone in a Stable Renal Transplant Recipient," Pharmacotherapy, 18(6):1356-1359 (1998).
Ostendorf, A. P. & Ng, Y-T., "Treatment-resistant Lennox-Gastaut syndrome: therapeutic trends, challenges and future directions," Neuropsychiatric Disease and Treatment, 13:1131-1140 (2017).
Panikasiwill, D. et al., "An endogenous cannabinoid (2-AG) is neuroprotective after brain injury," Nature 413:527-531 (2001).
Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf, 2 pages.
Pellicia, et al., International Association for Cannabis as Medicine, IACM 3rd Conference on Cannabinoids in Medicine, Sep. 9-10, 2005, 2005, Conference on Cannabinoids in Medicine, 72 pages.
Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.
Perucca, "Cannabinoids in the Treatment of Epilepsy: Hard Evidence at Last?" Journal of Epilepsy Research, 7(2):61-76 (2017).
Pertwee, "Cannabinoid receptor ligands: clinical and neuropharmacological considerations, relevant to future drug discovery and development," Expert Opin Investig Drugs, 9(7):1553-71 (2000).
Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol., 153(2):199-215 (2008).
Pertwee, "The Pharmacology and Therapeutic Potential of Cannabidiol," Cannabinoids, Chapter 3, DiMarzo, V. (Ed.), pp. 32-83 (2004).
Petrocellis, et al., "Effects of cannabinoids and cannabinoid-enriched Cannabis extracts on TRP channels and endocannabinoid metabolic enzymes," British Journal of Pharmacology, 163: 1479-1494 (2011).
Physician's Desk Reference, 63rd Ed., 2009, 423-461, 2192-2194, 2639-2242, 3019-3022.
Pohl, et al., "Effects of flunarizine on Metrazol-induced seizures in developing rats, " Epilepsy Res., 1(5):302-5 (1987).
Porter et al., "Report of a parent survey of cannabidiol-enriched cannabis use in pediatric treatment- resistant epilepsy," Epilepsy Behav., 29(3):574-577 (2013).
Porter et al., "Randomized, multicenter, dose-ranging trial of retigabine for partial-onset seizures," Neurology, 68(15):1197-1204 (2007).
Potter, "Cannabis Horticulture," Chapter 4, Handbook of Cannabis, ed. Roger G. Pertwee, pp. 65-88 (2014).
Potter, C., "Cannabis Extract Brings Hope for Children with Epilepsy," Dec. 3, 2013, 3 pages.
Poortman-Van Der Meer, "A contribution to the improvement of accuracy in the quantitation of THC," Forensic Science International, Apr. 1999, 101(1):1-8.
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://www.ctvnews.ca/health/health-headlines/pot-or-not-why-parents-of-kids-with-epilepsy-want-access-to-marijuana-treatment-1.1372695?cache =.
Pouton, "Lipid formulations for oral administration of drugs: non-emulsifying, self-emulsifying and 'self-micro emulsifying' drug delivery systems," Eur J Pharm Sci, 11(Suppl. 2):S93-S98 (2000).
Press, et al., "Parental reporting of response to oral cannabis extracts for treatment of refractory epilepsy," Epilepsy Behav. Apr. 2015;45:49-52. doi: 10.1016/j.yebeh.2015.02.043. Epub Apr. 3, 2015.
Pruitt et al., "Ethanol in Liquid Preparations Intended for Children," Pediatrics, 73(3):405-407 (1984).
Purcarin, G. & Ng, Y -T., "Experience in the use of clobazam in the treatment of Lennox-Gastaut syndrome," Ther Adv Neurol Disord 2014, vol. 7(3):169-176.
Raab et al., "Multiple myeloma," Lancet, 374(9686):324-339 (2009).
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ragona, et al., "Dravet syndrome: early clinical manifestations and cognitive outcome in 37 Italian patients," Brain Dev., 32:71-77 (2010).
Ramantani, et al. "Epilepsy in Aicardi-Goutieres syndrome," Official J Eur Paediatric Neurology Society, 18:30-37 (2014).
Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HTIA receptors are involved in the cannabidiol-induced attenuation of behavioural and cardiovascular responses to acute restraint stress in rats," Br J Pharmacol. Jan. 2009; 156(1): 181-8.
Rohrback, Brian G., Ph.D, MBA President of Infometrix, Inc. presents his talk on "Assays of Cannabinoids," at NYU School of Medicine's Cannabidiol Conference (Oct. 4, 2013). Video published online. <http://faces.med.nyu.edu/research-education/cannabidiol-conference>, 29 pages.
Romano et al., "Inhibition of colon carcinogenesis by a standardized Cannabis sativaextract with high content of cannabidiol," Phytomedicine, 21:631-639 (2014).
Rosenberg et al., "Cannabinoids and Epilepsy," Neurotherapeutics, 12(4):747-768 (2015).
Rosenkrantz et al., "Oral and Parenteral Formulations of Marijuana Constituents," J Pharm Sci, 61(7):1106-1112 (1972).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Russo, "Taming THC: potential cannabis synergy and phytocannabinoid-termoid entourage effects," British J. of Pharm. 1333 (2011), 21 pages.
Russo et al., "Pharmacology of Epileptogenesis and Related Comorbidities in the WAG/Rij Rat Model of Genetic Absence Epilepsy," Journal of Neuroscience Methods, 310:54-62 (2018).
Russo et al., "Upholding WAG/Rij Rats as a Model of Absence Epileptogenesis: Hidden Mechanisms and a New Theory on Seizure Development," Neuroscience and Biobehavioral Reviews, 71:388-408 (2016).
Rubio, et al. "In vivo Experimental Models of Epilepsy," Central Nervous System Agents in Medicinal Chemistry, 10:298-309, 2010.
Saade, D. & Joshi, C., "Pure Cannabidiol in the Treatment of Malignant Migrating Partial Seizures in Infancy: A Case Report," Pediatric Neurology, 52:544-547 (2015); http://dx.doi.org/10.1016/j.pediatrneurol.2015.02.008.
Sadanandasarma et al., Rasatarangini. 11th Ed. 1979:720-3. Sanskrit, 8 pages.
Samanta, D., "Cannabidiol: A Review of Clinical Efficacy and Safety in Epilepsy," Pediatric Neurology, 96:24- 29 (2019).
Sander, "The epidemiology of epilepsy revisited." Curr Opin Neural. Apr. 2003; 16(2): 165-70.
Sarkisova et al., "The WAG/Rij Strain: A Genetic Animal Model of Absence Epilepsy with Comorbidity of Depression," Progress in Neuro-Psychopharmacology & Biological Psychiatry, 35 854-876 (2011).
Sastri et al., Anandakandam. 1st Edition. 1952:241. Sanskrit, 5 pages.
Schafroth, M. A. et al., "Stereodivergent Total Synthesis of Δ9-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.

(56) References Cited

OTHER PUBLICATIONS

Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Scuderi et al., "Cannabidiol in medicine: a review of its therapeutic potential in CNS disorders," Phytother Res., 23(5):597-602 (2009).
Shih, J. J. et al., "Epilepsy treatment in adults and adolescents: Expert opinion, 2016," Epilepsy & Behavior, 69:186-222 (2017).
Shukla. [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Position Statement on the Use of Medical Cannabis for the Treatment of Epilepsy in Canada," Can J. Neurol. Sci., 33:783-786 (2006).
Silva, R. et al., "Clobazam as Add-on Therapy in Children with Epileptic Encephalopathy," Can. J. Neurol. Sci., 33:209-213 (2006).
Smith, R. M., "Identification of Butyl Cannabinoids in Marijuana," Journal of Forensic Sciences, 42:610-618 (1997).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414 (2006).
Subduction Coffee + Hemp, Product Page, 2023, 5 pages; https://subductioncoffee.com/?afmc=2j&utm_campaing=2j&utm_source=leaddyno&utm_medium=affiliate.
Sun et al., "Comparative study of organic solvent and water-soluble lipophilic extractives from wheat straw I: yield and chemical composition," J Wood Sci, 49:47-52 (2003).
Smith, R. M. & Kempfert, K. D., "Δ1-3,4-CIS-Tetrahydrocannabinol in Cannabis Sativa," Phytochemistry, 16:1088-1089 (1977).
Specchio, L. M. & Beghi, E., "Should Antiepileptic Drugs Be Withdrawn in Seizure-Free Patients?" CNS Drugs, 18(4):201-212 (2004).
Stewart, K., "Families migrating to Colorado for a medical marijuana miracle," Nov. 11, 2013, 8 pages; https://archive.sltrib.com/article.php?id=57052556&itype=CMSID.
Stinchcomb, A. L. et al., "Human skin permeation of Δ8-tetrahydrocannabinol, cannabidiol and cannabinol," JPP 2004, 56: 291-297.
Thiel, E. A., "Managing Epilepsy in Tuberous Sclerosis Complex," J Child Neurol 2004; 19:680-686.
"University of Utah doctors: Say 'yes' to cannabis oil for kids," By Kirsten Stewart The Salt Lake Tribune, Nov. 13, 2013, 4 pages.
Vanstraten, A.F. et al., "Update on the Management of Lennox-Gastaut Syndrome," Pediatric Neurology, 47:153-161 (2012).
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi,seizures%20stopped%20for%20seven%20days.&text=The%20marijuana%20strain%20Charlotte%20and,has%20been%20named%20after%20her.
Stephenson, "In Memoriam: Professor Jean Aicardi (1926-2015)," Pediatric Neurology, Jan. 2016, 54:3-4.
Stott et al., "Cannabinoids for the pharmaceutical industry," Euphytica, 140:83-93 (2004).
Strickley, "Solubilizing Excipients in Oral and Injectable Formulations," Table VIII, Pharmaceutical Research, 21(2):201-230 (2004).
Study NCT02224690—A Study to Investigate the Efficacy and Safety of Cannabidiol (*GWP42003-P; CBD*) AS Adjunctive Treatment for Seizures Associated With Lennox-Gastaut Syndrome in Children and Adults, Aug. 22, 2014; https://clinicaltrials.gov/ct2/show/NCT02224690, 1 page.
Swann et al., The effects of seizures on the connectivity and circuitry of the developing brain. Ment Retard Dev Disabil Res Rev. 2004; 10(2):96-100.
Tanya Lewis, Mystery Mechanisms, The Scientist Magazine, Jul. 29, 2016, 2 pages; http://www.the-scientist.com/.
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thomas et al., "Cannabidiol displays unexpectedly high potency as an antagonist of CB1 and CB2 receptor agonists in vitro," British J Pharmacology, 150(5):613-623 (1988).
Thompson et al., "Comparison of acute oral toxicity of cannabinoids in rats, dogs and monkeys, " Toxicology and Applied Pharmacology, vol. 25, Issue 3, pp. 363-372 (1973).
Thurman et al., "Standards for epidemiologic studies and surveillance of epilepsy," Epilepsia, 52 (Suppl 7):2-26 (2011).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurstone, "Avoid Charlotte's Web for Epilepsy," Jun. 26, 2014, URL <http://drthurstone.com/charlotted- web-not-safest-option-epilepsy-treatment/>, 4 pages.
Tose, L. V. et al., "Isomeric separation of cannabinoids by UPLC combined with ionic mobility mass spectrometry (TWIM-MS)—Part I," International Journal of Spectrometry, 418:112-121 (2017).
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Trost, B. M. & Dogra, K., "Synthesis of (-)-Δ9-trans-Tetrahydrocannabinol: Stereocontrol via Mo-Catalyzed Asymmetric Allylic Alkylation Reaction," Organic Letters, 9(5):861-863 (2007).
Turkanis et al., "An Electrophysiological Analysis of the Anticonvulsant Action of Cannabidiol on Limbic Seizures in Conscious Rats," Epilepsia., 20:351-363 (1979).
Uliss et al., "The conversion of 3,4-CIS- to 3,4-TRANS-cannabinoids," Tetrahedron, 34:1885-1888 (1978).
Usami et al., "Synthesis and pharmacological evaluation in mice of halogenated cannabidiol derivatives," Chem Pharm Bull (Tokyo), 47(11):1641-1645 (1999).
Unimed Pharmaceuticals, Inc., "Marinol®," Jul. 2006 <https://www.accessdata.fda.gov/dmgsatfda docs/label/2006/018651 s025s026lbl.pdf>, 11 pages.
Utah.gov [online), "2nd Agenda Controlled Substances Advisory Committee Meeting," Nov. 12, 2013, URL <https://www.utah.gov/pmn/files/81459.pdt>, 63 pages.
Van Bakel et al., "The draft genome and transcriptome of Cannabis sativa," Genome Biology 2011, 12:R102, 18 pages; http://genomebiology.com/2011/12/10/R102 (Oct. 24, 2011).
Van Rijckevorsel, "Treatment of Lennox-Gastaut syndrome: overview and recent findings," Neuropsychiatr Dis Treat. Dec. 2008; 4(6): 1001-1019.
Velasco et al., "Anticancer mechanisms of cannabinoids," Curr Oncol, 23(2):S23-S32 (2016).
Velisek, "Models of Chemically-Induced Acute Seizures," Models Seizure Epilepsy, 127-152 (2006).
Veliskova, Chapter 48 "Behavioral Characterization of Seizures in Rates," Model Seizures Epilepsy, 601-611 (2006).
Vollner et al., Haschisch XX: Cannabidivarin, ein neuer Haschisch-Inhaltsstoff. Tetrahedron Lett. 1969;10(3):145-7.
Wahle et al., "Development of tolerance to the anticonvulsant effect of valproate but not to ethosuximide in a rat model of absence epilepsy," Eur J Pharma. May 1990; 181(1-2):1-8.
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol. Sep. 28, 2001;428(1):51-7.
Warzak et al., "Caffeine Consumption in Young Children," The Journal of Pediatrics, vol. 158, Issue 3, P508-509, Mar. 1, 2011.
Weed Wars, Video I, Dec. 10, 2011, Weed Wars: The Story of Jayden-Andrew DeAngelo; https://www.youtube.com/watch?v=2WizdR5uHj0.
Weed Wars, Video II, May 25, 2013, 3 pages; available at https://www.youtube.com/watch?v=XBX_DB9sw5U.

(56) References Cited

OTHER PUBLICATIONS

Nathaniel Morris (of Weed Country on Discovery Channel), Selected Media Examples of Pediatric Applications of Cannabidiol, 2013, 6 pages; available at https://www.youtube.com/watch?v=Mw3wiWkbRg8.
Weimer-Kruel, A. et al., "Cannabidiol Interacts Significantly with Everolimus-Report of a Patient with Tuberous Sclerosis Complex," Neuropediatrics, 50(6), 2019, 4 pages; doi:https://doi.org/10.1055/s-0039-1695786.
Weston et al., "Tetrahydrocannabivarin exhibits anticonvulsant effects in a piriform cortical brain slice model of epileptiform activity." Pro British Pharm Soc 75th Anniv Meeting. Dec. 31, 2006 Found on: http://www.pA2on1ine.org/abstract/abstract.jsp?abid=28533. Abstract Only. 1 Page.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>, 30 pages.
"When to Expect Results from CW Hemp Oil", downloaded Sep. 5, 2017, https://www.cwhemp.com/blog/expecting-results-from-hemp, 9 pages.
Whittle et al., (2001). Prospects for New Cannabis-Based Prescription Medicines. Journal of Cannabis Therapeutics. 1(3-4); doi:10.1300/J175v01, 1(3-4), 23 pages.
Wilkey, R., "Weed Wars': Five-Year-Old Takes Medical Marijuana on Reality Show (VIDEO)", Dec. 10, 2011, 7 pages; https://www.huffpost.com/entry/weed-wars-five-year-old-smokes-marijuana_n_1140351.
Wikipedia.org [online], "Cannabinoid," Wikipedia, Apr. 2003, retrieved on Mar. 1, 2017, URL <https://en.wikipedia.org/wiki/Cannabinoid>, 15 pages.
Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal, rats%20in%20just%20eight%20 weeks, 5 pages.
Wingerchuk, "Cannabis for medical purposes: cultivating science, weeding out the fiction," Lancet. Jul. 24-30, 2004;364(9431):315-6.
Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p. 0240 Abstract, 1 page.
Yamaori, S. et al., "Potent inhibition of human cytochrome P450 3A isoforms by cannabidiol: Role of phenolic hydroxyl groups in the resorcinol moiety," Life Sciences, 88:730-736 (2011).
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, 63:35-47 (2014).
Zhornitsky & Potvin, "Cannabidiol in Humans—The Quest for Therapeutic Targets," Pharmaceuticals, 5:529-552 (2012).
Zhao et al., "Chapter 27: Repetitive Seizures in the Immature Brain," Models of Seizures and E[epilepsy, 341-350 (2006).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
U.S. Appl. No. 62/154,660, filed Apr. 29, 2015, Vangara et al.
Notice of Opposition to European Patent Application No. EP18737374.1, Patent No. EP3641819, dated Jul. 12, 2024, 23 pages.
Notice of Opposition to European Patent Application No. EP19702670.1, Patent No. EP3743053, dated Aug. 27, 2024, 22 pages.
Abati, E. et al., "Cannabidiol treatment of refractory epileptic spasms: an open label study," American Epilepsy Society, Annual Meeting, Abstract 3.404, 2015, 2 pages; https://aesnet.org/abstractslisting/cannabidiol-treatment-of-refractory-epileptic-spasms--an-open-label-study.
Aagaard, L. et al., "Adverse Drug Reactions in the Paediatric Population in Denmark: A Retrospective Analysis of Reports Made to the Danish Medicines Agency from 1998 to 2007," Drug Saf, 33(4):327-339 (2010).
Actiq™ (Oral Transmucosal Fentanyl Citrate), Clinical Pharmacology and Biopharmaceutics Review, Reviewer Suresh Doddapaneni, Ph.D., Center for Drug Evaluation and Research, Application No. NDA 20747, Submission Date: Nov. 11, 1996, Review Date: Apr. 22, 1997, 25 pages.
Aker, R. G. et al., "Chemically Induced Experimental Models of Absence Epilepsy," Chemical-Induced Seizures: Mechanisms, Consequences and Treatment, Chapter 6, 2011, pp. 67-79.
Allen, J. W., "Clobazam as an adjunctive treatment in refractory epilepsy," British Medical Journal, 286:1246-1247 (1983).
Anderson, C. L., "An Evaluation of Effectivness of Cannabidiol as an Antiepileptic Drug for Children with Intractable Generalized Epilepsy," Dissertation, University of Florida, 2017, 130 pages; https://ufdc.ufl.edu/UFE0050852/00001/pdf.
Advagraf 0.5 mg prolonged-release hard capsules, Advagraf 1 mg prolonged-release hard capsules, Advagraf 3 mg prolonged-release hard capsules, Advagraf 5 mg prolonged-release hard capsules, Annex 1—Summary of Product Characteristics, retrieved on Aug. 13, 2024, 6 pages.
Arik, A. E. et al., "Effect of levetiracetam on penicillin induced epileptic activity in rats," Acta Neurobiol Exp, 74:266-275 (2014).
[No Author Listed], "Photo Release—Kannaway Back office Goes Live CBD-Rich Hemp Oil Products Offered for Sale," May 7, 2014, Globe Newswire, https://www.globenewswire.com/en/news-release/2014/05/07/634020/30927/en/Photo-Release-Kannaway-Back-Office-Goes-Live-CBD-Rich-Hemp-Oil-Products-Offered-for-Sale.html, 6 pages.
[No Author Listed], GW and Otsuka Enter into Gobal Cannabinoid Research Collaboration, News Release, Jul. 9, 2007; https://www.otsuka.co.jp/en/company/newsreleases/2007/20070709_1.html, 4 pages.
[No Author Listed], License Agreement between GW Pharma and GW Pharmaceuticals, PLC and Otsuka, Feb. 2007; https://www.sec.gov/Archives/edgar/data/1351288/000104746913003351/a2213875zex-10_16.htm, 63 pages.
Andre, E. S. et al., "Spontaneous absence-like activity in Wistar rats: Behavioral and electrographic characteristics and the effects of antiepileptic drugs," Acta Scientiarum. Biological Sciences, 36(2):231-239 (2014).
Astruc-Diaz, F., "Cannabinoids delivery systems based on supramolecular inclusion complexes and polymeric nanocapsules for treatment of neuropathic pain," Université Claude Bernard—Lyon I, 2012, submitted on Jan. 23, 2014; https://tel.archives-ouvertes.fr/tel-00935588 [accessed Nov. 1, 2019], 278 pages.
Bacca, A., "HempVap from HempMedsPX," Mar. 10, 2014; https://cannabisnow.com/hempvap-from-hempmedspx/, 3 pages.
Barton, M. E. et al., "Pharmacological characterization of the 6 Hz psychomotor seizure model of partial epilepsy," Epilepsy Research, 47:217-227 (2001).
Ben-Ari, Y., "Seizures Beget Seizures: The Quest for GABA as a Key Player," Critical Reviews in Neurobiology, 18(1-2):135-144 (2006).
Bhattacharyya, S. et al., "Opposite Effects of delta-9-Tetrahydrocannabinol and Cannabidiol on Human Brain Function and Psychopathology," Neuropsychopharmacology, 35:764-774 (2010).
Bialer, M. & White, S., "Key factors in the discovery and development of new antiepileptic drugs," Nat Rev Drug Discov, 9(1):68-82 (2010); doi: 10.1038/nrd2997.
Bijnsdorp, I. V. et al., "Analysis of Drug Interactions," Chapter 34, Cancer Cell Culture, Methods in Molecular Biology, Second Edition, Ian A. Cree, Ed., 2011:731:421-34, 19 pages.
Bowman et al., "Epilepsy," Encyclopedia of Life Sciences, 1, 2001; www.els.net, 8 pages.

(56) References Cited

OTHER PUBLICATIONS

Bromfield, E. B., Cavazos, J. I., Sirven (Ed.,), An Introduction to Epilepsy [Internet], West Hartford, CT, American Epilepsy Society; 2006, PMID: 20821849, 187 pages.
Carlini, E. A. et al., "Anticonvulsant Activity of Four Oxygenated Cannabidiol Derivatives," Research Communications in Chemical Pathology and Pharmacology, 12(1), Sep. 1975, 15 pages.
Chesney et al., "Adverse effects of cannabidiol: a systematic review and meta-analysis of randomized clinical trials," Neuropsychopharmacol., 45:1799-1806 (2020); https://doi.org/10.1038/s41386-020-0667-2.
Cholongitas et al., "Systematic review: The model for end-stage liver disease—should it replace Child-Pugh's classification for assessing prognosis in cirrhosis?" Aliment Pharmacol Ther, 22(11-12): 1079-89 (2005); doi: 10.1111/j.1365-2036.2005.02691.x . . . .
Chou, T. -C., "Drug Combination Studies and Their Synergy Quantification Using the Chou-Talalay Method," Cancer Res, 70(2):440-446 (2010).
Ciszek, M., "Once- Versus Twice-daily Tacrolimus: Are the Formulations Equivalent?" Central European Journal of Urology, 66(3):350-351 (2013).
ClinicalTrials.gov archive, History of Changes for Study: NCT02324673, National Institute of Health U.S. National Library of Medicine (Dec. 19, 2014), https://classic.clinicaltrials.gov/ct2/history/NCT02324673?V_1=View#StudyPageTop, 13 pages.
Consroe, P. & Wolkin, A., "Cannabidiol—antiepileptic drug comparisons and interactions in experimentally induced seizures in rats," J Pharmacol Exp Ther. Apr. 1977;201(1):26-32.
Consroe et al., "Antiepileptic Potential of Cannabidiol Analogs," J Clin Pharmacol., 21:428S-436S (1981).
Consroe et al., "Assay of Plasma Cannabidiol by Capillary Gas Chromatography/Ion Trap Mass Spectroscopy Following High-Dose Repeated Daily Oral Administration in Humans," Pharmacology Biochemistry & Behavior, 40:517-522 (1991).
Costa, B. et al., "Oral anti-inflammatory activity of cannabidiol, a non-psychoactive constituent of cannabis, in acute carrageenan-induced inflammation in the rat paw," Naunyn-Schmiedeberg's Arch Pharmacol, 369:294-299 (2004).
Crowther et al., "The Medication of Cannabis," The transcript of a Witness Seminar held by the Wellcome Trust Centre for the History of Medicine at UCL, London, on Mar. 24, 2009; http://qmro.qmul.ac.uk/xmlui/handle/123456789/2822, 90 pages.
Devarbhavi, "An update on drug-induced liver injury," J. Clinical and Experimental Hepatology, 2(3):247-259 (2012).
De Deyn et al., "Chemical models of epilepsy with some reference to their applicability in the development of anticonvulsants," Epilepsy Research, 12:87-110 (1992).
DeRosa et al., "Chapter XI: Epilepsy," Significant Pharmaceuticals Reported in US Patents, 1st Edition, May 2007, 10 pages.
Devinsky et al., Trial Protocol, Supplementary Material to "Trial of Cannabidiol for Drug-Resistant Seizures in the Dravet Syndrome," N Engl J Med, 376(21):2011-2020 (2017), 426 pages.
Devinsky et al., "Cannabidiol efficacy independent of clobazam: Meta-analysis of four randomized controlled trials," Acta Neurol Scand., 142:531-540 (2020).
Dos Santos, R. G. et al., "Phytocannabinoids and epilepsy," Journal of Clinical Pharmacy and Therapeutics, 40:135-143 (2015).
Epidiolex® (cannabidiol) oral solution, CV, Prescribing Information, 2021, 38 pages; https://www.accessdata.fda.gov/drugsatfda_docs/label/2021/210365Orig1s011lbl.pdf.
Epidiolex® (cannabidiol) oral solution, CV, Prescribing Information, 2024, 32 pages; https://pp.jazzpharma.com/pi/epidiolex.en.USPI.pdf.
Epidyolex 100 mg oral soluction, Summary of Product Characteristics, European Medicines Compendium, Sep. 2019, 19 pages; https://web.archive.org/web/20200920022105/https://www.medicines.org.uk/emc/product/10781/smpc.
Evans, Randolph W., Neurology Case Studies, Neurol Clin 24, xi-xii, 2006, 2 pages.
Fabiano, V. et al., "Adverse drug reactions in newborns, infants and toddlers: pediatric pharmacovigilance between present and future," Expert Opinion on Drug Safety, 11(1): 95-105 (2011); doi: 10.1517/14740338.2011.584531.
FDA Guidance for Industry: Botanical Drug Development, U.S. Dept. of Health and Human Services: Food and Drug Administration, Dec. 2016, 34 pages.
FDA Guidance for Industry: Q11 Development and Manufacture of Drug Substances, U.S. Dept. of Health and Human Services: Food and Drug Administration, Nov. 2012, 36 pages.
FDA Good Review Practice: Clinical Review of Investigational New Drug Applications, Office of New Drugs in the Center for Drug Evaluation and Research at the Food and Drug Administration, Dec. 2013, 113 pages.
FDA Guidance for Industry on Drug-Induced Liver Injury: Premarketing Clinical Evaluation, Food and Drug Administration, Jul. 30, 2009, 4 pages.
Feierman, D. E. & Lasker, J. M., "Metabolism of fentanyl, a synthetic opioid analgesic, by human liver microsomes. Role of CYP3A4," Drug Metabolism and Disposition, 24(9):932-939, Sep. 1996, Abstract. https://dmd.aspetjournals.org/content/24/9/932, 4 pages.
Fryar, C. D. et al., Anthropometric reference data for children and adults: United States, 2011-2014, National Center for Health Statistics. Vital Health Statistics, 3(39), 2016, 46 pages.
French, J. A. et al., "Adjunctive everolimus therapy for treatment-resistant focal-onset seizures associated with tuberous sclerosis (EXIST-3): a phase 3, randomised, double-blind, placebo-controlled study," Lancet, 388:2153-2163 (2016).
Gaber et al., "Conversion from Twice-daily Tacrolimus Capsuled to Once Daily Extended Release Tacrolimus(LCPT): a Phase 2 Trial of Stable Renel Transplant Recipients," Transplantation, 96(2):191-197 (2013); doi: 10.1097/TP.0b013e3182962cc1.
Galetin et al., "Multisite Kinetic Analysis of Interactions Between Prototypical CYP3A4 Subgroup Substrates: Midazolam, Testosterone, and Nifedipine," Drug Metabolism and Disposition, 31(9):1108-1116 (2003).
Gaston, T. E. et al., "Quality of life in adults enrolled in an open-label study of cannabidiol (CBD) for treatment-resistant epilepsy," Epilepsy & Behavior, 95:10-17 (2019).
Gaston, T. E. et al., "Cannabis for the Treatment of Epilepsy: an Update," Curr Neurol Neurosci Rep., 18(11):73 (2018), 9 pages; doi: 10.1007/s11910-018-0882-y.
Gauthier et al., "Clobazam: A Safe, Efficacious, and Newly Rediscovered Therapeutic for Epilepsy," CNS Neurosci Ther., 21(7):543-548 (2015); doi: 10.1111/cns.12399. Epub Apr. 28, 2015.
Gedde & Maa, "Whole Cannabis Extract of High Concentration Cannabidiol May Calm Seizures in Highly Refractory Pediatric Epilepsies," American Epilepsy Society, 67th Annual Meeting, Dec. 6-10, 2013. Abstract, 1 page.
Gemmill, R. M. et al., "Synergistic growth inhibition by Iressa and Rapaymycin is modulated by VHL mutations in renal cell carcinoma," British Journal of Cancer, 92:2266-2277 (2005).
Goldenberg, M. M., "Overview of Drugs Used for Epilepsy and Seizures," P & T, 35(7):392-415 (2010).
Greaves et al., "First Dose of Potential New Medicines to Humans: How Animals Help," Nature Reviews Drug Discovery, 3:226-236 (2004).
Gunning et al., "Cannabidiol in conjunction with clobazam: analysis of four randomized controlled trials," Acta Neurol Scand., 143:154-163 (2021).
Gupta, S., "Why I changed my mind on weed," Aug. 8, 2013; https://www.cnn.com/2013/08/08/health/gupta-changed-mind-marijuana/index.html, 8 pages.
Ha et al., "Epilepsy: Treatment and Management," US Pharm., 38(1):35-39 (2013).
Hancock, E. C. & Cross, J. H., "Treatment of Lennox-Gastaut syndrome (Review)," Cochrane Database of Systematic Reviews, 2013, Issue 2. Art. No. CD003277, doi: 10.1002/14651858.CD003277.pub3., 35 pages.
Hazenkamp, A. et al., "Quantitative Analysis of Cannabinoids from *Cannabis sativa* Using H-NMR," Chem. Pharm. Bull., 52(6):718-721 (2004).

(56) References Cited

OTHER PUBLICATIONS

Hazenkamp, A., "Cannabis; extracting the medicine," Doctoral Thesis, 1976, Proefschrift Universiteit Leiden; https://extractionmagazine.com/wp-content/uploads/2018/06/Cannabis-extracting-the-medicine-Arno-Hazekamp-Thesis.pdf, 187 pages.
Hussain et al., "Perceived efficacy of cannabidiol-enriched cannabis extracts for treatment of pediatric epilepsy: A potential role for infantile spasms and Lennox-Gastaut syndrome," Epilepsy & Behavior, 47:138-141 (2015).
Ilegal Trailer, YouTube video, Mar. 27, 2014; https://www.youtube.com/watch?v=CtJJ1pzMKxs, 5 pages.
Insys Therapeutics Submits Drug Master File for Cannabidiol Active Pharmaceutical Ingredient (API), Marketwired, May 29, 2014; https://www.biospace.com/article/releases/insys-therapeutics-submits-drug-master-file-for-cannabidiol-active-pharmaceutical-ingredient-api-/, 5 pages.
Insys Therapeutics Commences Dosing in Phase 1/2 Safety and Pharmacokinetic Study of Cannabidiol Oral Solution in Pediatric Epilepsy Patients, BioSpace (Apr. 23, 2015); https://www.biospace.com/article/releases/insys-therapeutics-commences dosing-in-phase-1-2-safety-and-pharmacokinetic-study-of-cannabidiol-oral-solution-in-pediatric epilepsy-patients-/, 3 pages.
Insys Therapeutics, Inc., Quarterly Report Form Q-10, U.S. Securities and Exchange Commission, Mar. 31, 2014; insy20140331_10q.htm, 42 pages.
Insys Therapeutics, Inc., Corporate Integrity Agreement and Conditional Exclusion Release, 2014, 100 pages.
Kelley, "Medical Cannabis Community Wants to Remain Apart," Kitsap Peninsula Business Journal, Apr. 3, 2013; available at https://www.420magazine.com/community/threads/medical-cannabis-community-wants-to-remain-apart. 186955/, 4 pages.
Klonopin® Tablets (clonazepam) Klonopin® Wafers (clonazepam orally disintegrating tablets) Product Label, revised Apr. 4, 2009, 18 pages.
Kobayashi T., et al., "Renal Carcinogenesis, Hepatic Hemangiomatosis and Embryonic Lethality Caused by a Germ-Line Tsc2 Mutation in Mice," Cancer Research, 59:1206-1211 (1999).
Koek et al., "Treatment-refractory posttraumatic stress disorder (TRPTSD): a review and framework for the future," Progress in Neuro-Psychopharmacology & Biological Psychiatry, 70:170-218 (2016).
Labroo et al., "Fentanyl metabolism by human hepatic and intestinal cytochrome P450 3A4: implications for interindividual variability in disposition, efficacy, and drug interactions," Drug Metab Dispos, 25(9):1072-80 (1997).
Leite et al., "New insights from the use of pilocarpine and kainate models," Epilepsy Research, 50:93-103 (2002).
Lodzki et al., "Cannabidiol-transdermal delivery and anti-inflammatory effect in a murine model," Journal of Controlled Release, 93:377-387 (2003).
Manini et al., "Safety and Safety and Pharmacokinetics of Oral Cannabidiol When Administered Concomitantly With Intravenous Fentanyl in Humans," J Addict Med., 9(3): 204-210 (2015);. doi:10.1097/ADM.0000000000000118.
Mead et al., "The Untold Story of the Cannabidiol (CBD) Revolution," US Neurology, 2018; 14(Suppl. 3):2-8. Published Online: Oct. 16, 2018.
Mechoulam et al., "Hashish-I: The Structure of Cannabidiol," Tetrahedron, 19:2073-2078 (1963).
Morrison et al., "A Phase 1 Investigation Into the Potential Effects of Cannabidiol on CYP3A4-Mediated Drug-Drug Interactions in Healthy Volunteers," Abstract No. 1.297, Submission ID: 500033, Presentation Date: Dec. 1, 2018, Published Date: Nov. 5, 2018; https://aesnet.org/abstractslisting/a-phase-1-investigation-into-the-potential-effects-of-cannabidiol-on-cyp3a4-mediated-drug-drug-interactions-in-healthy-volunteers, 2 pages.
Morrison et al., "A Phase 1, Open-Label, Pharmacokinetic Trial to Investigate Possible Drug-Drug Interactions Between Clobazam, Stiripentol, or Valproate and Cannabidiol in Healthy Subjects," Clinical Pharmacology in Drug Development, 8(8):1009-1031 (2019).
Mudigoudar et al., "Emerging Antiepileptic Drugs for Severe Pediatric Epilepsies," Semin Pediatr Neurol, 23:167-179 (2016).
[No Author Listed], European Medicines Agency (EMA), "Public summary of opinion on orphan designation - Cannabidiol for the treatment of Dravet syndrome," Nov. 10, 2014, https://www.ema.europa.eu/en/documents/orphandesignation/eu3141339-public-summary-opinion-orphan-designation-cannabidiol-treatment-dravetsyndrome-en.pdf, 4 pages.
Palmer, A. C. et al., "Combination Cancer Therapy Can Confer Benefit via Patient-to-Patient Variability without Drug Additivity or Synergy," Cell, 171:1678-1691 (2017).
Patsalos et al., "Clinical implications of trials investigating drug-drug interactions between cannabidiol and enzyme inducers or inhibitors or common antiseizure drugs," Epilepsia, 61:1854-1868 (2020).
Pertwee, "Cannabidiol as a potential medicine," In: Mechoulam, R. (eds) Cannabinoids as Therapeutics. Milestones in Drug Therapy MDT (2005), pp. 47-65, Birkhäuser Basel. https://doi.org/10.1007/3-7643-7358-X_3.
Rison, R. A., "How to write a neurology case report," Journal of Medical Case Reports, 10:91 (2016); doi: 10.1186/s13256-016-0867-x, 5 pages.
Rosenkrantz et al., "Inhalation, Parenteral and Oral LD50 Values of $\Delta^9$-Tetrahydrocannabinol in Fischer Rats," Toxicology and Applied Pharmacology, 28:18-27 (1974).
Rosenkrantz et al., "Toxicity of Short-Term Administration of Cannabinoids to Rhesus Monkeys," Toxicology and Applied Pharmacology, 58:118-131 (1981).
Samara et al., "Pharmacokinetics of Cannabidiol in Dogs," Drug Metabolism and Disposition, 16(3):469-472 (1988).
Sands, T. T. et al., "Long-Term Safety, Tolerability, and Efficacy of Cannabidiol in Children with Refractory Epilepsy: Results from an Expanded Access Program in the US," CNS Drugs, 33:47-60 (2019); https://doi.org/10.1007/s40263-018-0589-2.
Sasidharan, S. et al., "Extraction, Isolation and Characterization of Bioactive Compounds from Plants' Extracts," Afr J Tradit Complement Altern Med., 8(1):1-10 (2018).
Schafroth et al., "Δ9-cis-Tetrahydrocannabinol: Natural Occurrence, Chirality, and Pharmacology," Journal of Natural Products, 84:2502-2510 (2021).
Schwieterman, M. L. et al., "Strawberry Flavor: Diverse Chemical Compositions, a Seasonal Influence, and Effects on Sensory Perception," PLoS One, 9(2): e88446 (2014); doi: 10.1371/journal.pone.0088446, 12 pages.
Serra I., et al., "Cannabidiol modulates phosphorylated rpS6 signalling in a zebrafish model of Tuberous Sclerosis Complex," Behavioural Brain Research, 363:135-144 (2019).
Sirven et al., Finding the Best Dosage of Medication, Epilepsy Foundation (Mar. 19, 2014); https://www.epilepsy.com/treatment/medicines/finding-best-dosage, 11 pages.
Sluss, R. J., "Comparison of Artificial Flavors in Commercial Products and Actual Natural Flavor via Gas Chromatography Mass Spectroscopy Data." (2009). Electronic Theses and Dissertations. Paper, 1804; https://dc.etsu.edu/etd/1804, 72 pages.
Smith et al., "A1-3-cis-Tetrahydrocannabinol in Cannabis Sativa," Phytochemistry, 16:1088-1089 (1977).
Tang et al., "Application of Machine-learning Models to Predict Tacrolimus Stable Dose in Renal Transplant Recipients," Scientific Reports, 8(7):42192 (2017), 10 pages; doi: 10.1038/srep42192.
Thomas et al., "Characterization of the Lipophilicity of Natural and Synthetic Analogs of $\Delta^9$-Tetrahydrocannabinol and Its Relationship to Pharmacological Potency," The Journal of Pharmacology and Experimental Therapeutics, 255(2):624-630 (1990).
Thompson et al., "Oral and Intravenous Toxicity of $\Delta^9$-Tetrahydrocannabinol in Rheus Monkeys," Toxicology and Applied Pharmacology, 27:648-665 (1974).
Turkanis et al., "Excitatory and Depressant Effects of Delta-9-Tetrahydrocannabidinol and Cannabidiol on Cortical Evoked Responses in the Conscious Rat," Psychopharmacology, 75:294-298 (1981).
Vezyroglou, K. & Cross, J. H., "Targeted Treatment in Childhood Epilepsy Syndromes," Curr Treat Options Neurol, 18:29 (2016), Published online May 7, 2016. doi: 10.1007/s11940-016-0407-4, 12 pages.

(56) References Cited

OTHER PUBLICATIONS

Vrielynck, P., "Current and emerging treatments for absence seizures in young patients," Neuropsychiatric Disease and Treatment, 9:963-975 (2013).

Weed Country, Episode 5, 2013; https://www.youtube.com/watch?v=0isjCcMtxBk; https://www.youtube.com/watch?v=GitMYGvwC4E&t=212s, 25 pages.

Weed Country, Episode 6, 2013; https://www.youtube.com/watch?v=Uyzuy1fNQfQ, 18 pages.

Wheless, J. W et al., "Pharmacokinetics and Tolerability of Multiple Doses of Pharmaceutical-Grade Synthetic Cannabidiol in Pediatric Patients with Treatment-Resistant Epilepsy," CNS Drugs, 33(6):593-604 (2019); doi: 10.1007/s40263-019-00624-4.

Willis, L., "Final Report on the Safety Assessment of Sesame Oil," Journal of the American College of Toxicology, 12(3):261-277 (1993).

Wirrell, E. C., "Treatment of Dravet Syndrome," Can J Neurol Sci., 43: S13-S18 (2016).

Zhang, T. et al., "Pre-seizure state identified by diffuse optical tomography," Scientific Reports, 4:3798 (2014); https://doi.org/10.1038/srep03798, 10 pages.

Zuardi et al., "Antipsychotic Effect of Cannabidiol," J Clin Psychiatry, 56(10): 485-486 (1995).

Zuardi et al., "Cannabidiol for the treatment of psychosis in Parkinson's disease," Journal of Psychopharmacology, 23(8):979-983 (2009).

Zuardi A., et al., "Inverted U-Shaped Dose-Response Curve of the Anxiolytic Effect of Cannabidiol during Public Speaking in Real Life," Frontiers in Pharmacology, 8, Article 259, pp. 1-9 (2017).

Barlina, R. et al., "Chapter 30 —Chemistry and composition of coconut oil and its biological activities," Multiple Biological Activities of Unconventional Seed Oils, pp. 383-395 (Mar. 2022); https://doi.org/10.1016/B978-0-12-824135-6.00025-8.

Citti et al., "Analysis of impurities of cannabidiol from hemp. Isolation, characterization and synthesis of cannabidibutol, the novel cannabidiol butyl analog," Journal of Pharmaceutical and Biomedical Analysis, 175:112752; https://doi.org/10.1016/j.jpba.2019.112752 (Jul. 2019), 13 pages.

Cunetti, L. et al., "Chronic Pain Treatment with Cannabidiol in Kidney Transplant Patients in Uruguay," Transplantation Proceedings, vol. 30 (Suppl. 2): 390-576 (Mar. 2017), 1 page.

Dravet et al., "Chapter 65—Dravet syndrome (severe mycolonic epilepsy in infancy)," Handbook of Clinical Neurology, 111:627-633 (Jan. 2013).

Elsohly et al., "Synthetic cannabinoids: Analysis and metabolites", Life Sciences, vol. 97, Issue 1, pp. 78-99 (Feb. 2014).

Herlopian, A. et al., "Cannabidiol in treatment of refractory epileptic spasms: An open label study," Epilepsy & Behavior, 106:106988 (Mar. 2020), 7 pages; https://doi.org/10.1016/j.yebeh.2020.106988.

Lainez-Aguirre et al., "A Stochastic Optimization approach for the design of Individualized Dosage Regimens", Aiche J., 59: 3296-3307 (Mar. 2013).

Namayandeh et al., "Olive and Sesame Oil Effect on Lipid Profile in Hypercholesterolemie Patients, Which Better?", vol. 4, No. 9, September, pp. 1059-1062. (Sep. 2013).

Nazario et al., "Caffeine protects against memory loss induced by high and non-anxiolytic dose of cannabidiol in adult zebrafish (Danio rerio)," Pharmacol Biochem Behav, 135:210-6 (Jun. 2015); doi: 10.1016/j.pbb.2015.06.008. Epub Jun. 20, 2015.

[No Author Listed] Children's Hospital of Philadelphia. Dravet Syndrome. Retrieved from the Internet on Jan. 8, 2025, https://www.chop.edu/ conditions-diseases/dravet-syndrome#:~:text=Dravet%20syndrome%20%E2%80%94%20formerly%20known%20as,and%20differences%20in%20childhood%20development., 2025, 5 pages. [month of publication unknown].

Pawar et al., "Issues in the Formulation of Drugs for Oral Use in Children", Pediatr Drugs, 4: 371-379 (Aug. 2012).

Timmings et al., "Lamotrigine as an Add-On Drug in the Management of Lennox-Gastaut Syndrome," European Neurology, 32(6):305-307 (May 1992).

Wanleenuwat, P. et al., "Antibiotic-induced epileptic seizures: mechanisms of action and clinical considerations," Seizure—European Journal of Epilepsy, 81:167-174 (Oct. 2020). doi: 10.1016/j.seizure.2020.08.012. Epub Aug. 14, 2020.

Scheffer, I.E. et al., "Dravet syndrome or genetic (generalized) epilepsy with febrile seizures plus?" Brain & Development, 394-400 (May 2009).

Sun, G -q. et al., "Benzodiazepines or related drugs and risk of pneumonia: A systematic review and meta-analysis," Int J Geriatr Psychiatry, 34:513-521 (Jan. 2019).

* cited by examiner

* Primary Analysis ** Sensitivity Analysis $ Excluded from primary and sensitivity PK analysis @ Excluded from sensitivity analysis only Geometric means for the primary analysis and sensitivity analysis for the reference treatment are the same.

* Primary Analysis ** Sensitivity Analysis $ Excluded from primary and sensitivity PK analysis @ Excluded from sensitivity analysis only Geometric means for the primary analysis and sensitivity analysis for the reference treatment are the same.

ALP, alkaline phosphatase; ALT, alanine aminotransferase; AST, aspartate aminotransferase; GGT, gamma-glutamyl transferase; TBL, total bilirubin

USE OF CANNABIDIOL IN THE TREATMENT OF EPILEPSY

CROSS-REFERENCE TO RELATED APPLICATIONS

This application is a U.S. National Phase application, filed under U.S.C. § 371(c), of International Application No. PCT/GB2021/051520, filed Jun. 16, 2021, which claims priority to, and the benefit of, United Kingdom Patent Application No. 2009321.7, filed Jun. 18, 2020. Each of these documents is incorporated by reference herein in its entirety for all purposes.

FIELD OF THE INVENTION

The present invention relates to the use of cannabidiol (CBD) in the treatment of patients with childhood-onset epilepsy who are concurrently taking caffeine.

Where the CBD is used in combination with caffeine, caution should be taken. For example, the dose of either the CBD and/or caffeine may be required to be reduced. Moreover, the patient may need to be monitored for side effects of said drug-drug interaction.

Preferably the CBD used is in the form of a highly purified extract of *cannabis* such that the CBD is present at greater than 95% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

BACKGROUND TO THE INVENTION

The *cannabis* plant (*Cannabis sativa* L.) produces trichomes that synthesize a large number of pharmacologically active compounds called phytocannabinoids. The most abundant of these are THC and CBD, although the amounts and proportions of the various phytocannabinoids in each plant vary by strain and can be adjusted by breeding.

Epidiolex is a liquid formulation of botanically derived, highly purified CBD extract that has been developed for use as a treatment for various orphan paediatric epilepsy syndromes, characterised in that the patients are deemed to be treatment-resistant on one or more anti-epileptic drugs (AEDs) (see WO 2019/97238 and WO 2016/203239). The drug has been approved for the treatment of seizures associated with Dravet syndrome and Lennox-Gastaut syndrome. It is formulated from extracts prepared from *Cannabis sativa* L. plants that have a defined chemical profile and contain consistent levels of CBD as the principal phytocannabinoid. Extracts from these plants are processed to yield pure (>95 to >98% w/w) CBD. The pure CBD is subsequently dissolved in excipients with added sweetener and flavouring.

Due to the above-outlined use of CBD in medicine, this has necessitated understanding different interactions CBD may have with other medicines or drugs. Drug-drug interactions (DDIs) are one of the commonest causes of medication error and can both induce the development of adverse drug reactions or reduce the clinical efficacy.

Caffeine is the world's most widely consumed psychoactive drug. It is a central nervous system stimulant of the methylxanthine class. It is found in the seeds, nuts and leaves of a number of different plants, including: *Coffea*

*Arabica* (used for coffee), Thea *sinensis* (used for tea), Cola *acuminata* (used as a nut, tea or in soft drinks including cola), *Theobroma cacao* (used in cocoa and chocolate) and *Paulinia cupana* (used as guarana in snack bars and energy drinks)'. Effects of caffeine include feeling more alert and active, as well as being more restless and excitable. It was reported in a 2010 Pediatrics journal study that a significantly high percentage of children, 75%, consume caffeine on a daily basis[2]. Such a high percentage means that it is vital to understand the effects of caffeine and CBD co-consumption, as there may be a significant overlap between children consuming caffeine and young patients being administered their prescribed CBD-based medication.

Previous anecdotal reports have suggested synergistic effects of CBD and caffeine. The authors of these reports claim that the combination of CBD and caffeine can remove the jittery edge that a caffeine hit often brings, as well as feelings of anxiety and nausea[3,4]. In fact, several companies have commercialized CBD-infused coffee, for example Green Roads CBD Coffee and Teas and Subduction Coffee+ Hemp[6]. However, such commercially available supplies and anecdotal reports use low doses of CBD (~30 mg per serving), not nearly as high as the therapeutic doses in Epidiolex used to treat Dravet Syndrome and Lennox-Gastaut Syndrome. Epidiolex is prescribed for use at doses of 10-20 mg/kg/day, therefore a 40 kg child may be taking doses of up to 800 mg/day. Clearly in a heavier child or adolescent even higher doses such as 1500 mg/day could be taken.

The most common types of DDIs involve the inhibition or induction of one or more drug-metabolizing enzymes by a drug. When inhibitors or inducers of a particular drug-metabolizing enzyme are coadministered with a drug that is metabolized by that enzyme, the pharmacokinetic parameters of one or both drugs change, leading to increased or decreased drug exposures. It is this change in exposure that may result in adverse events, depending on the level of exposure, and doses may have to be changed. Dosing modifications are unpredictable because reducing a dose too much risks undertreating the patients, but over-dosing can increase exposure to potentially dangerous levels.

Elevated levels of CBD are known to cause transaminase elevation, rash, somnolence, sedation, lethargy, diarrhoea, pyrexia, weight decrease, nasopharyngitis, irritability, oropharyngeal pain, and decreased appetite. Transaminase elevations can lead to hepatic dysfunction, including unexplained nausea, vomiting, right upper quadrant abdominal pain, fatigue, anorexia, or jaundice and/or dark urine. Elevated exposure of caffeine exposure is known to cause insomnia, nervousness and restlessness, stomach irritation, nausea and vomiting, increased heart rate and respiration, and other side effects. The present disclosure reduces the incidence of one or more of the above side effects.

The pharmacological properties of CBD are not fully elucidated. As indicated on the FDA approved label for EPIDIOLEX®, CBD is metabolized in the liver and the gut by CYP2C19 and CYP3A4 enzymes, and UGT1A7, UGT1A9, and UGT2B7 isoforms. CBD inhibits uridine 5'-diphospho-glucuronosyltransferase (UGT) enzymes UGT1A9 and UGT2B7. CBD is reported to be an inhibitor of CYP2B6, CYP2C8, CYP2C9, and CYP2C19. Data also suggest that CBD inhibits CYP3A4. CBD may induce or inhibit CYP1A2 and CYP2B6 at clinically relevant concentrations. However, it is not known if CBD is a strong, moderate, or weak inhibitor, or indeed if CBD-mediated inhibition of any of these enzymes produces a clinically significant result. Samanta (2019)[7] further suggests CBD may induce or inhibit CYP1A2 activity, identifying caffeine as a substrate of CYP1A2, but does not present any evidence towards inhibition or induction. The present invention discloses clinically significant biochemical findings in several subjects during the trial: elevations in liver enzymes (ALT, AST, and GGT).

The present invention describes data from healthy subjects who received a single dose of caffeine after having taken repeated doses of CBD during an open-label, Phase 1 clinical trial. It was found that CBD increased the levels of caffeine in the subject's blood. Such an interaction is unexpected and as such the use of these drugs in combination should be done with close monitoring of the patient.

Furthermore, in the same study it was observed that administration of CBD in doses commonly administered to DS and LGS patients (approx. 20 mg/kg/day) to healthy adults resulted in elevations in liver chemistries consistent with drug induced liver injury (DILI). Such a finding was surprising as such high elevations in healthy volunteers has previously not been observed.

BRIEF SUMMARY OF THE DISCLOSURE

In accordance with a first aspect of the present invention there is provided cannabidiol (CBD) for use in the treatment of childhood-onset epilepsy in patients who are concurrently taking caffeine characterised in that the blood levels of caffeine and associated markers are monitored to ensure the levels do not become toxic.

In a further embodiment of the invention the blood levels of liver enzymes are additionally monitored. These enzymes ALT, AST, and GGT are markers associated with drug induced liver injury (DILI). Higher than normal levels of liver enzymes may be present when CBD and caffeine are coadministered.

Preferably, the dose of CBD is lowered. Alternatively, the dose of caffeine is lowered. More preferably the dose of CBD and caffeine are lowered.

Preferably, the CBD is in the form of a highly purified extract of *cannabis* which comprises at least 95% (w/w) CBD, which comprises less than 0.15% THC and up to 1% CBDV. Alternatively, the CBD is present as a synthetic compound.

Preferably, the lowered dose of CBD ranges from about 5 mg/kg/day to about 20 mg/kg/day. Alternatively, the dose of caffeine is lowered to below 200 mg/day.

An average cup of coffee comprises approximately 95 mg of caffeine and therefore a patient may inadvertently consume doses of caffeine which exceed safe levels without realizing and as such blood levels should be monitored during treatment.

Preferably, the childhood-onset epilepsy is: Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

In accordance with a second aspect of the present invention there is provided a method of treating childhood-onset epilepsy in an individual in need thereof, comprising administering to the patient a therapeutically effective amount of cannabidiol with caution, wherein the individual is taking caffeine concurrently.

Preferably the said caution comprises lowering the dose of cannabidiol. Alternatively, the said caution comprises lowering the dose of caffeine.

Preferably the said caution comprises monitoring said individual for side effects.

More preferably the said caution further comprises discontinuing cannabidiol if said side effects are observed.

More preferably still the said caution comprises advising said individual of side effects from said concurrent therapy.

BRIEF DESCRIPTION OF THE DRAWINGS

Embodiments of the invention are further described hereinafter with reference to the accompanying drawings, in which.

DEFINITIONS

Figure 1:
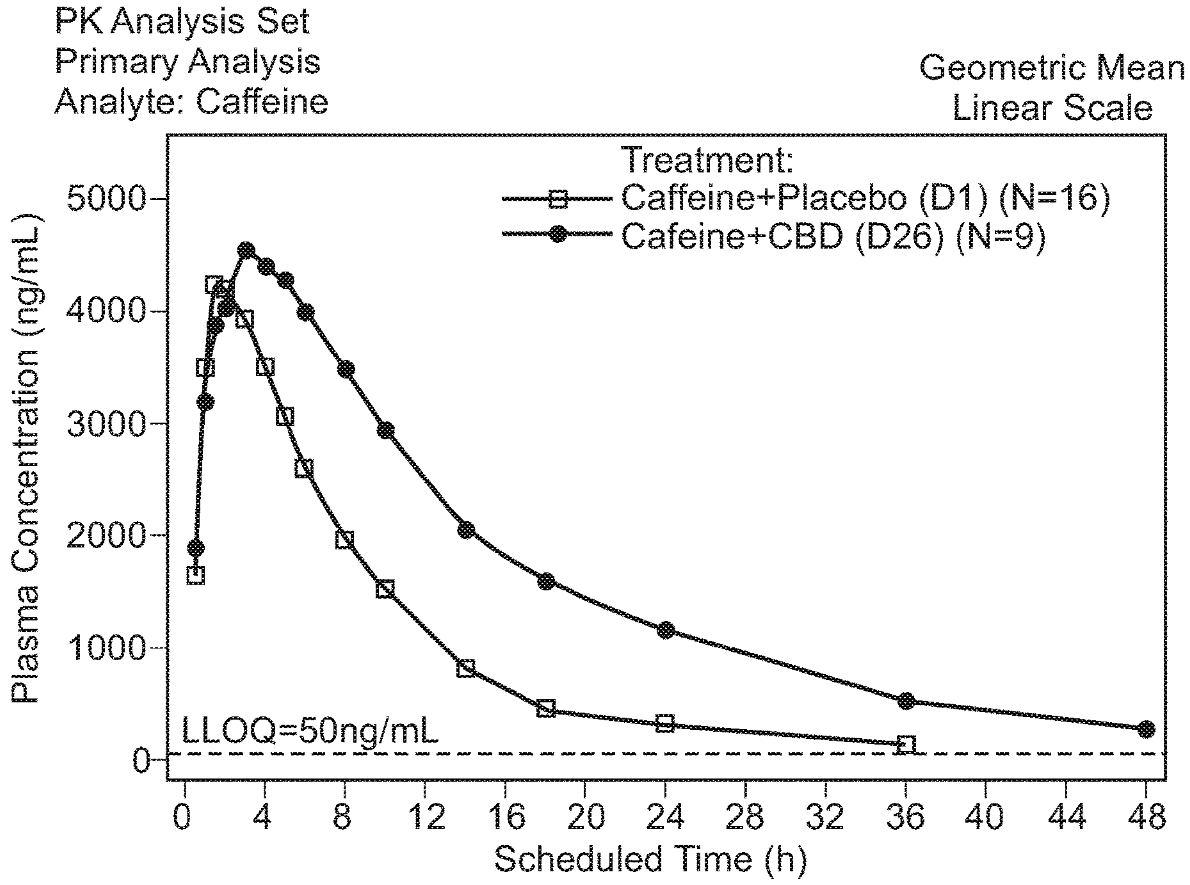
FIG. 1 shows Geometric Mean Plasma Concentrations of Caffeine Following Administration of Caffeine+Placebo (Day 1) and of Caffeine+CBD (Day 26) on a linear scale.

Definitions of some of the terms used to describe the invention are detailed below:

The cannabinoids described in the present application are listed below along with their standard abbreviations.

TABLE 1

| Cannabinoids and their abbreviations | | |
|---|---|---|
| CBD | Cannabidiol | 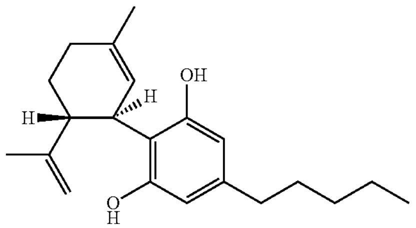 [SMILES: C=C(C)[C@@H]1CCC(C)=C[C@H]1c1c(O)cc(CCCCC)cc1O] |

TABLE 1-continued

| Cannabinoids and their abbreviations | | |
| --- | --- | --- |
| CBDA | Cannabidiolic acid | 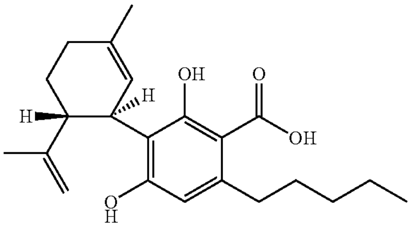 [SMILES: C=C(C)[C@@H]1CCC(C)=C[C@H]1c1c(O)cc(CCCCC)c(C(=O)O)c1O] |
| CBDV | Cannabidivarin | 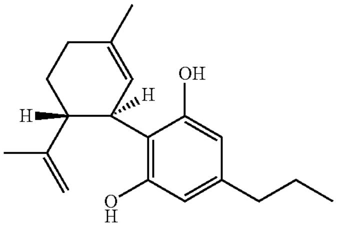 [SMILES: C=C(C)[C@@H]1CCC(C)=C[C@H]1c1c(O)cc(CCC)cc1O] |
| CBDVA | Cannabidivarinic acid | 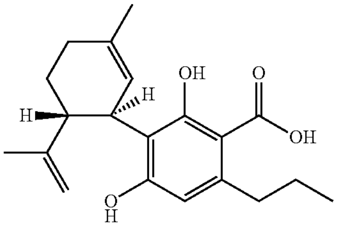 [SMILES: C=C(C)[C@@H]1CCC(C)=C[C@H]1c1c(O)cc(CCC)c(C(=O)O)c1O] |
| THC | Tetrahydrocannabinol | 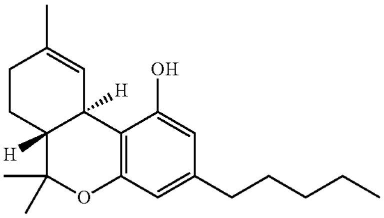 [SMILES: CCCCCc1cc(O)c2c(c1)OC(C)(C)[C@@H]1CCC(C)=C[C@@H]21] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 95% (w/w) pure. The highly purified cannabinoid extract may be purified further such that the cannabinoid content is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; tuberous sclerosis complex; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

$C_{max}$ is the maximum observed plasma concentration.

$t_{max}$ is the time to attain maximum observed plasma concentration.

$AUC_{0-\infty}$ is the area under the plasma concentration-time curve from time 0 to infinity, calculated as $AUC_{0-28}=AUC_{0-t}+\hat{C}_{last}/k_{el}$, where $\hat{C}_{last}$ is the estimated last plasma concentration and where $k_{el}$ is the terminal phase rate constant.

$AUC_{0-t}$ is the area under the plasma concentration-time curve up to time t, where t is the last point with a concentration above the lower limit of quantification (LLOQ).

Clinical laboratory measurements of liver injury and function, the Upper Limit of Normal (ULN) values used are: 68 international units [IU]/L for ALT, 45 IU/L for aspartate aminotransferase (AST), 129 IU/L for alkaline phosphatase (ALP), 29 μmol/L for total bilirubin (TBL), and 59 IU/L for gamma-glutamyl transferase (GGT).

Drug induced liver injury (DILI) is when serum ALT exceeds 5×ULN.

DETAILED DESCRIPTION OF THE INVENTION

Preparation of Highly Purified Cbd Extract

The following describes the production of the highly-purified (>95-98% w/w) cannabidiol extract which has a known and constant composition was used in the Examples below.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD. Although the CBD is highly purified because it is produced from a *cannabis* plant rather than synthetically there is a small number of other cannabinoids which are co-produced and co-extracted with the CBD. Details of these cannabinoids and the quantities in which they are present in the medication are as described in Table 2 below.

TABLE 2

Composition of highly purified CBD extract

| Cannabinoid | Concentration |
|---|---|
| CBD | >95-98% w/w |
| CBDA | NMT 0.15% w/w |
| CBDV | NMT 1.0% w/w |
| $\Delta^9$ THC | NMT 0.15% w/w |
| CBD-C4 | NMT 0.5% w/w |

>—greater than
NMT—not more than

EXAMPLE 1: A PHASE 1, OPEN-LABEL, PHARMACOKINETIC DRUG-DRUG INTERACTION TRIAL TO INVESTIGATE THE EFFECT OF CANNABIDIOL ON THE PHARMACOKINETICS (PK) OF CAFFEINE

Primary Objectives: To investigate the effect of CBD treatment following repeated dosing on the PK of a single dose of caffeine in healthy subjects.

Primary Endpoints: The primary PK parameters were: $AUC_{0-\infty}$, $AUC_{0-t}$, $C_{max}$, and $t_{max}$, for caffeine. The PK parameter endpoints, derived from the plasma concentration-time profiles of caffeine on Day 1 administered with placebo and the PK parameter endpoints derived from a single dose of caffeine in participants at steady state CBD following 13 days of CBD, 20 mg/kg twice daily (b.i.d).

Secondary Objectives: To evaluate the safety and tolerability of CBD when given with a single dose of caffeine in healthy subjects.

Secondary Endpoints: Safety includes: incidence and severity of adverse events (AEs), incidence of laboratory abnormalities based on hematology, clinical chemistry, and urinalysis test results; 12-lead electrocardiogram (ECG) parameters, vital sign measurements, physical examinations, Columbia-Suicide Severity Rating Scale (C-SSRS) questionnaire scores; the PK parameter endpoints, derived from the plasma concentration-time profiles of caffeine on Day 1 administered with placebo and the PK parameter endpoints derived from a single dose of caffeine in participants at steady state CBD following 13 days of CBD, 20 mg/kg twice daily (b.i.d).

Design: This was a phase 1, open-label, single site trial to investigate the effect of multiple dose administration of CBD on the PK of caffeine in healthy subjects. The duration of the trial was approximately 10 weeks, which includes a screening period (up to 4 weeks), a treatment period (4 weeks) and a safety follow-up period (2 weeks). After signing the informed consent form (ICF), participants entered the screening period (Day −28 to −1). On Day −1, which is the day prior to Day 1, the first day of IMP (caffeine+placebo) administration, screened participants who continued to meet eligibility criteria were admitted to the clinical research unit (CRU). The subjects were resident in the CRU for 2 periods. Subjects were administered a concurrent dose of 7.5 mL of placebo oral solution and 200 mg caffeine on Day 1, 30 minutes after starting a standardized breakfast. They were discharged on Day 3 after completion of the assessments. On Day 3, the first dose of CBD was taken in the morning in the CRU, and on this day, the escalating doses of CBD were dispensed to subjects to be taken at home from Day 4 to Day 12. After discharge on Day 3, the subjects returned to the CRU for ambulatory visits on Days 12, 18, and 23. At these ambulatory visits, the maintenance doses of CBD were dispensed to subjects to be taken at home from Day 13 to Day 25 (the evening dose of Day 25 was taken in the CRU). The subjects were admitted again to the CRU in the afternoon of Day 25. On Days 26 and 27, subjects received CBD b.i.d, and on Day 26, a single oral dose of caffeine was given concurrently with the morning dose of CBD. The subjects were discharged on Day 28 after completion of the assessments. The subjects had a follow-up visit 14 to 16 days after the last IMP dose. In addition to the scheduled follow-up visit, several subjects came back to the CRU after Day 28 for unscheduled visits for additional blood sampling regarding out-of-normal reference range values of liver enzymes. CBD and caffeine were administered as shown in Table 3.

TABLE 3

Treatment Schedule

| Day | Morning Dose | Evening Dose |
|---|---|---|
| 1 | 7.5 mL placebo oral solution (matched to CBD) 200 mg caffeine oral tablet | Not applicable |
| 3 | 250 mg CBD: 2.5 mL oral solution | Not applicable |
| 4-5 | 250 mg CBD: 2.5 mL oral solution | 250 mg CBD: 2.5 mL oral solution |
| 6-7 | 500 mg CBD: 5 mL oral solution | 250 mg CBD: 2.5 mL oral solution |
| 8-9 | 500 mg CBD: 5 mL oral solution | 500 mg CBD: 5 mL oral solution |
| 10-11 | 750 mg CBD: 7.5 mL oral solution | 500 mg CBD: 5 mL oral solution |
| 12-25 | 750 mg CBD: 7.5 mL oral solution | 750 mg CBD: 7.5 mL oral solution |

TABLE 3-continued

| Treatment Schedule | | |
|---|---|---|
| Day | Morning Dose | Evening Dose |
| 26 | 750 mg CBD: 7.5 mL oral solution 200 mg caffeine oral tablet | 750 mg CBD: 7.5 mL oral solution |
| 27 | 750 mg CBD: 7.5 mL oral solution | 750 mg CBD: 7.5 mL oral solution |

Formulation Mode of Administration, Dose, Regimen: The CBD formulation is an oral liquid formulation that is clear and colourless to yellow in appearance (100 mg/mL CBD in sesame oil with anhydrous ethanol, added sweetener (sucralose), and strawberry flavouring. The oral liquid formulation is administered with a syringe. The CBD formulation is taken b.i.d. 30 minutes after starting a standard meal. In this trial, a maximum dose of 750 mg CBD b.i.d was selected, considered a therapeutic dose in epilepsy patients.

The placebo is an oral liquid formulation (sesame oil and anhydrous ethanol with added sweetener [sucralose], and strawberry flavouring). The oral liquid formulation was administered with a syringe.

The caffeine is provided as a 50 mg tablet.

On Day 1 and Day 26, the IMP (caffeine and placebo on Day 1, and caffeine and CBD on Day 26) were taken between 08:00 hours and 09:00 hours. From Day 3 to Day 27, the morning dose of CBD was taken approximately at 08:00 h and the evening dose (not applicable on Day 3) was taken 12 hours later. Dosing for each individual subject was to be at around the same time (±1 hour) on each dosing day. The time of the morning dose on Day 26 matched the time of the morning dose on Day 1 (with a margin of ±5 minutes).

The use of all prescribed medication and all over-the-counter medication, vitamin preparations and other food supplements, or herbal medications was prohibited from first admission to the CRU until the follow-up visit. The use of methylxanthine-containing beverages or food (coffee, [iced] tea, cola, chocolate [milk], mocha drinks/sweets, energy drinks) was not allowed from first admission to the CRU until discharge on Day 28. Foods and beverages containing grapefruit, Seville oranges, pomelos, star fruit, or cranberries, or cruciferous vegetables were not allowed from first admission to the CRU until discharge on Day 28. Alcohol was not allowed from 48 hours prior to each admission to the CRU and throughout the inpatient period, and from 48 hours prior to the safety follow-up visit. Strenuous exercise was not allowed from 7 days prior to first admission to the CRU until the follow-up visit. Subjects were not to consume any foods containing poppy seeds within 72 hours (3 days) prior to each admission to the CRU as this could cause a false positive drug screen result. The use of tobacco- or nicotine-containing products was not allowed from first admission to the CRU until the follow-up visit.

Pharmacokinetic Assessments: Plasma concentrations of caffeine and its metabolite paraxanthine were determined on the following days: 1, 2, 3, 26, 27 and 28. Plasma concentration of CBD determined on the following days: 23, 25, and 26. These were determined using liquid chromatography and tandem mass spectrometry.

The following assessments were performed: demographics, medical history, physical examination, C-SSRS, vital signs, body weight, height, 12-lead ECG, adverse events (AEs), previous and concomitant medications recorded. Clinical laboratory samples including chemistry, hematology, serology, urine drug screen, alcohol test.

Trial subjects were sixteen healthy male and female subjects aged between 18 and 60. All 16 participants took at least 1 dose of trial drug; 9 (56%) completed treatment as planned and received the expected total dose of 400 mg caffeine and 31.25 g cannabidiol.

Results

Figure 2:
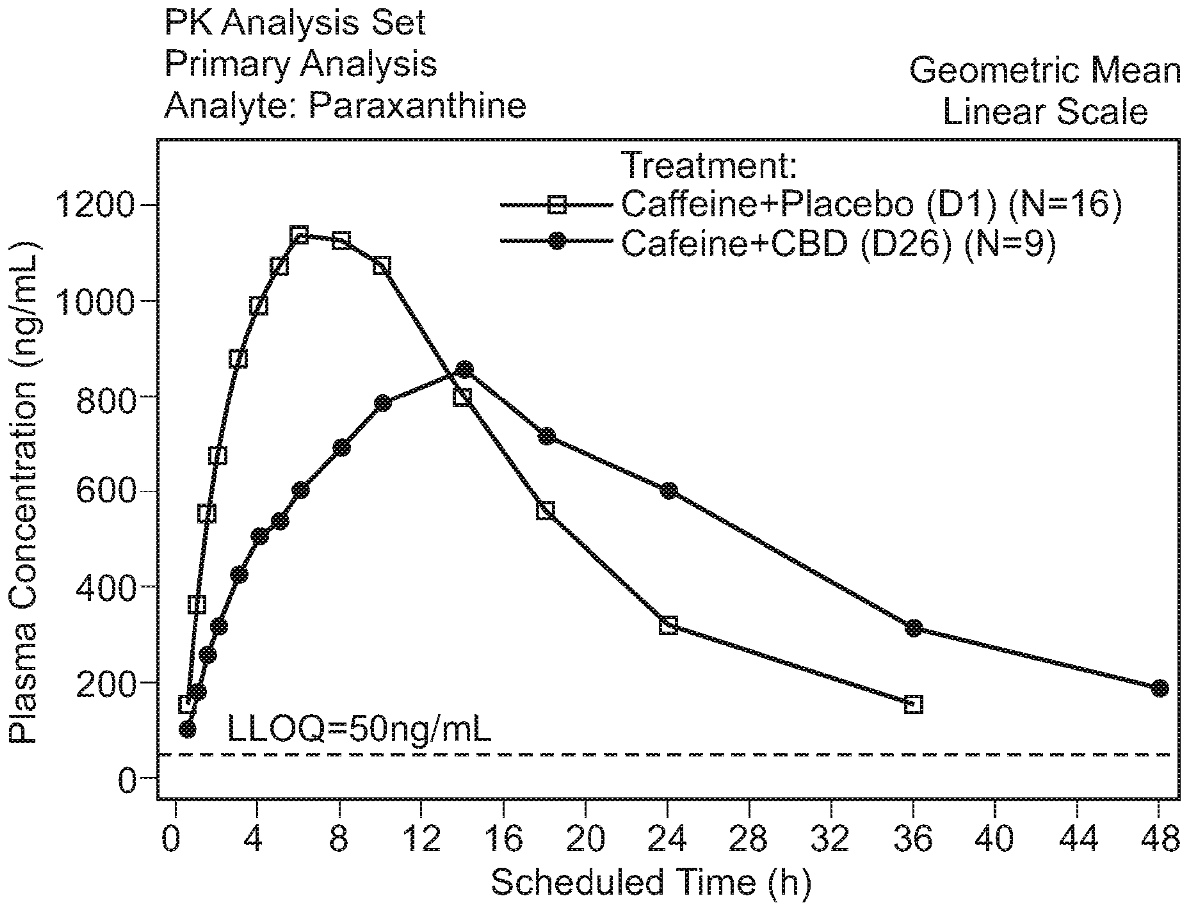
FIG. 2 shows Geometric Mean Plasma Concentrations of Paraxanthine Following Administration of Caffeine+Placebo (Day 1) and of Caffeine+CBD (Day 26) on a linear scale.

Plasma concentrations of caffeine and paraxanthine following administration of caffeine+placebo and of caffeine+CBD are presented in FIGS. 1 and 2.

Trough plasma samples for CBD were taken on Days 23, 25, and 26. Trough levels of CBD confirmed that CBD had reached steady state before caffeine and CBD were coadministered on Day 26.

After dosing with 200 mg caffeine and placebo on Day 1 and coadministration of 200 mg caffeine and 750 mg CBD on Day 26, caffeine and its metabolite paraxanthine were quantifiable in the majority of subjects at the first sampling time point, i.e., 0.5 hours.

On Day 1, following administration of 200 mg caffeine and placebo, maximum postdose geometric mean plasma concentrations were reached at 1.5 hours for caffeine and 6.0 hours for paraxanthine. On Day 26, following coadministration of 200 mg caffeine and 750 mg CBD, maximum postdose geometric mean plasma concentrations were reached at 3.0 hours for caffeine and 14.0 hours for paraxanthine.

As is apparent from the individual and geometric mean profiles, the elimination phase of caffeine and paraxanthine was multiphasic following 200 mg caffeine and 750 mg CBD coadministration on Day 26, and caffeine concentrations were higher and paraxanthine concentrations lower compared with administration of 200 mg caffeine and placebo on Day 1.

Figure 3:
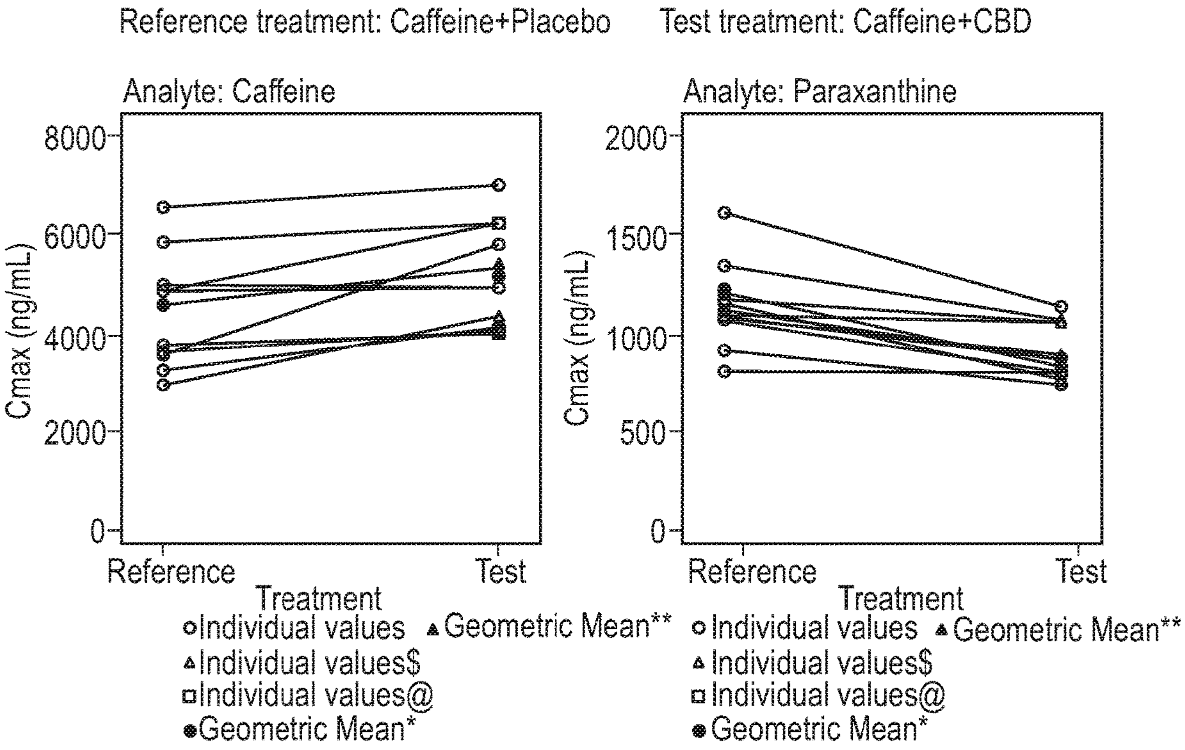
FIG. 3 shows Geometric Mean and Individual Subject $C_{max}$ for Caffeine and Paraxanthine Following Administration of Caffeine+Placebo (Day 1) and of Caffeine+CBD (Day 26).
Figure 4:
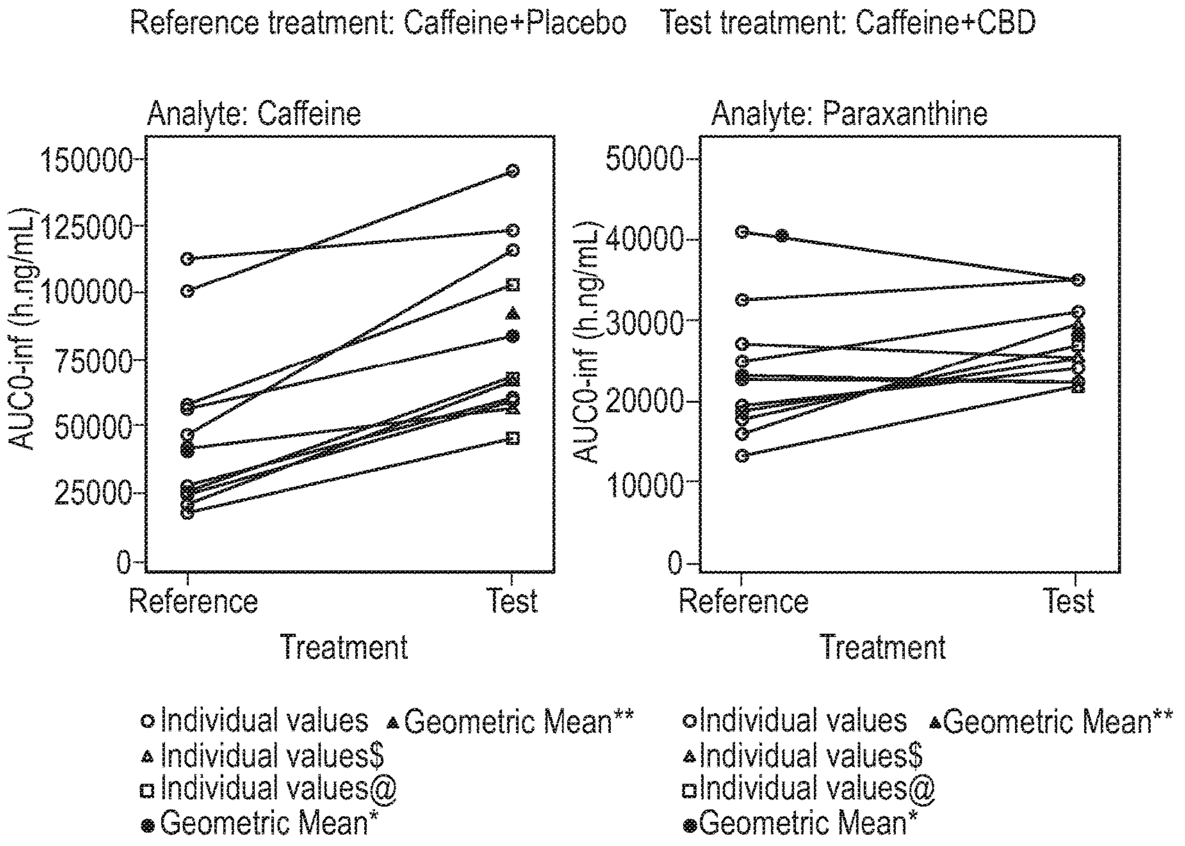
FIG. 4 shows Geometric Mean and Individual Subject AUC0-∞ for Caffeine and Paraxanthine Following Administration of Caffeine+Placebo (Day 1) and of Caffeine+CBD (Day 26).

The PK parameters for caffeine and paraxanthine are presented in Table 4. The differences between geometric mean and individual subject PK parameters for caffeine and paraxanthine following administration of caffeine+placebo (Day 1) and of caffeine+CBD (Day 26) are shown in FIGS. 3 ($C_{max}$) and 4 ($AUC_{0-\infty}$), and the statistical analyses of the differences in PK parameters are presented in Table 5.

TABLE 4

Summary of the Pharmacokinetic Parameters (Geometric Mean [Geometric CV %]) of Caffeine and Paraxanthine Following Administration of Caffeine + Placebo (Day 1) and of Caffeine + CBD (Day 26)

| Parameter | Primary Analysis: Caffeine + Placebo (Day 1) (N = 16) | Primary Analysis: Caffeine + CBD (D 26-FU) (N = 9) | Sensitivity Analysis: Caffeine + CBD (D 26-FU) (N = 6) |
|---|---|---|---|
| **Caffeine** | | | |
| $AUC_{0-t}$ (ng · h/mL) | 40000 (56.7) | 78300 (37.2) | 85500 (35.1) |
| $AUC_{0-\infty}$ (ng · h/mL) | 40900 (57.6) | 83400 (41.0) | 92300 (39.4) |
| $C_{max}$ (ng/mL) | 4600 (23.5) | 5170 (21.1) | 5430 (19.0) |
| $t_{max}^{a}$ (h) | 1.51 (0.50-3.00) | 3.00 (0.50-5.00) | 3.00 (0.50-4.13) |
| **Paraxanthine** | | | |
| $AUC_{0-t}$ (ng · h/mL) | 21500 (27.8) | 23900 (12.8) | 23900 (14.0) |
| $AUC_{0-\infty}$ (ng · h/mL) | 23000 (30.2) | 27900 (18.4) | 28100 (20.1) |
| $C_{max}$ (ng/mL) | 1230 (20.6) | 885 (15.8) | 894 (17.1) |
| $t_{max}^{a}$ (h) | 7.99 (4.00-18.02) | 14.00 (5.97-18.00) | 14.00 (10.00-18.00) |

FU = follow-up; max = maximum; min = minimum; PK = pharmacokinetic.
Note:
For the treatment of caffeine + placebo, the primary analysis and sensitivity analysis are equal.
[a]Median (min-max).

TABLE 5

Statistical Analysis of the Pharmacokinetic Parameters of Caffeine and Paraxanthine Following Administration of Caffeine + Placebo (Day 1) and of Caffeine + CBD (Day 26)

| Analyte | PK Parameter | Geometric LS Means: n | Reference | n | Test | Ratio Test/Reference: Estimate | 90% CI [Lower, Upper] |
|---|---|---|---|---|---|---|---|
| **Primary Analysis** | | | | | | | |
| Caffeine | $C_{max}^{a}$ (ng/mL) | 16 | 4600 | 9 | 5269 | 1.15 | [1.04, 1.26] |
| | $AUC_{0-t}^{a}$ (ng · h/mL) | 16 | 39969 | 9 | 75237 | 1.88 | [1.56, 2.27] |
| | $AUC_{0-\infty}^{a}$ (ng · h/mL) | 16 | 40856 | 9 | 79718 | 1.95 | [1.62, 2.35] |
| | $t_{max}^{b}$ (h) | 9 | 1.52 | 9 | 3.00 | 0.58 | [0.01, 1.50] |
| Paraxanthine | $C_{max}^{a}$ (ng/mL) | 16 | 1227 | 7 | 961 | 0.78 | [0.72, 0.86] |
| | $AUC_{0-t}^{a}$ (ng · h/mL) | 16 | 21454 | 7 | 23579 | 1.10 | [0.96, 1.26] |
| | $AUC_{0-\infty}^{a}$ (ng · h/mL) | 16 | 22972 | 7 | 27038 | 1.18 | [1.03, 1.35] |
| | $t_{max}^{b}$ (h) | 7 | 8.00 | 7 | 14.00 | 3.49 | [0.48, 6.00] |
| **Sensitivity Analysis** | | | | | | | |
| Caffeine | $C_{max}^{a}$ (ng/mL) | 16 | 4600 | 6 | 5460 | 1.19 | [1.03, 1.36] |
| | $AUC_{0-t}^{a}$ (ng · h/mL) | 16 | 39969 | 6 | 71265 | 1.78 | [1.39, 2.29] |
| | $AUC_{0-\infty}^{a}$ (ng · h/mL) | 16 | 40856 | 6 | 76272 | 1.87 | [1.45, 2.41] |
| | $t_{max}^{b}$ (h) | 6 | 2.25 | 6 | 3.00 | 0.57 | [0.00, 1.25] |
| Paraxanthine | $C_{max}^{a}$ (ng/mL) | 16 | 1227 | 6 | 984 | 0.80 | [0.73, 0.88] |
| | $AUC_{0-t}^{a}$ (ng · h/mL) | 16 | 21454 | 6 | 22526 | 1.05 | [0.93, 1.18] |
| | $AUC_{0-\infty}^{a}$ (ng · h/mL) | 16 | 22972 | 6 | 26023 | 1.13 | [0.99, 1.30] |
| | $t_{max}^{b}$ (h) | 6 | 8.00 | 6 | 14.00 | 3.99 | [−0.02, 7.00] |

CI = confidence interval; LS = least squares; PK = pharmacokinetic.
Note:
Reference, caffeine + placebo treatment; Test, caffeine + CBD treatment.
[a]AUC and $C_{max}$, the interaction effect was explored using a mixed effect (analysis of variance) model with treatment as fixed factor and subject as a random effect.
[b]$t_{max}$, nonparametric Wilcoxon signed-rank test presenting the Hodges-Lehman estimate and 90% CI based on the Tukey method. Median, median of the difference, and approximate 90% CI for the difference are presented.

For caffeine, as shown by the point estimates for the treatment ratios (primary analysis) in Table 5, when compared with caffeine and placebo (Day 1), coadministration of caffeine and CBD (Day 26) resulted in a slight increase in $C_{max}$ (1.15, 90% CI: [1.04, 1.26]) and a larger increase in $AUC_{0-t}$ (1.88, 90% CI: [1.56, 2.27]) and $AUC_{0-\infty}$ (1.95, 90% CI: [1.62, 2.35]). The $t_{max}$ for caffeine was later after administration of caffeine and CBD (Day 26) compared with caffeine and placebo administration (Day 1) (difference Hodges-Lehman estimate: 0.58, 90% CI: [0.01, 1.50]).

For paraxanthine, as shown by the point estimates for the treatment ratios (primary analysis), when compared with caffeine and placebo (Day 1), coadministration of caffeine and CBD (Day 26) resulted in a decrease in $C_{max}$ (0.78, 90% CI: [0.72, 0.86]) and a slight increase in $AUC_{0-t}$ (1.10, 90% CI: [0.96, 1.26]) and $AUC_{0-\infty}$ (1.18, 90% CI: [1.03, 1.35]). The $t_{max}$ for paraxanthine tended to be later after administration of caffeine and CBD (Day 26) compared with caffeine and placebo administration (Day 1) (difference Hodges-Lehman estimate: 3.49, 90% CI: [0.48, 6.00]).

Similar results were seen for the primary and sensitivity analyses.

Thus, exposure to caffeine increased by 15% for $C_{max}$ and 95% for $AUC_{0-\infty}$ when caffeine was given with steady-state CBD compared to when caffeine was given with placebo.

Exposure to the CYP1A2-mediated caffeine metabolite paraxanthine was impacted by CBD coadministration as evidenced by a 22% decrease in $C_{max}$ and 18% increase in $AUC_{0-\infty}$. The $t_{max}$ for paraxanthine was delayed when caffeine was coadministered with CBD, which may reflect a slower formation of the metabolite.

Figure 5:
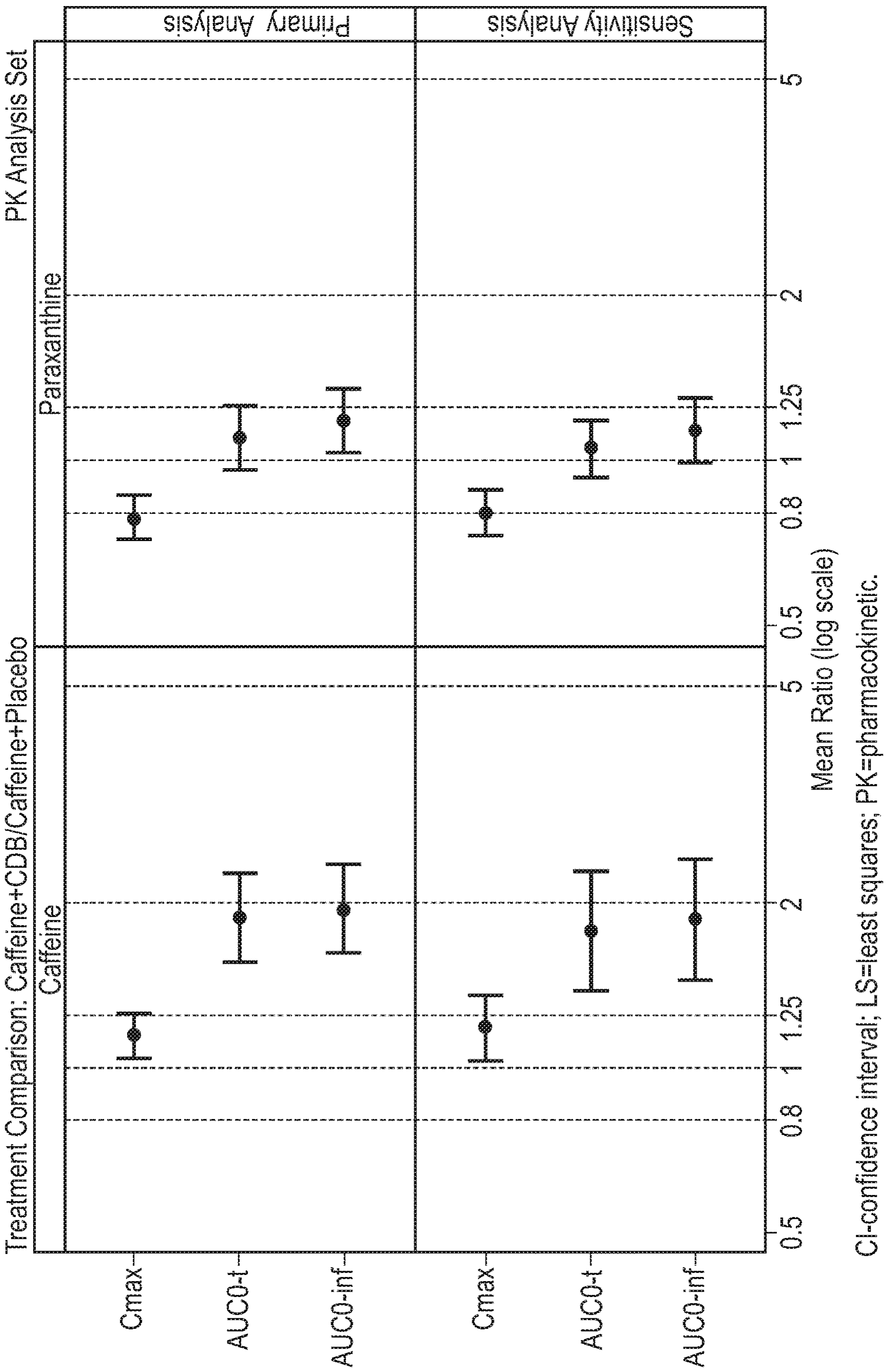
FIG. 5 shows Geometric LS Mean Ratio and 90% CI Showing the Effect of Steady-state CBD on Exposure to Caffeine and Paraxanthine.

FIG. 5 provides a visual summary of the results of the primary PK endpoint for the trial, illustrating the point estimates for the ratio of the geometric LS means and the 90% CI for exposure to caffeine and paraxanthine when subjects were administered caffeine in the presence of steady-state CBD compared with administration of caffeine and placebo.

Coadministration of caffeine and CBD resulted in a change in caffeine and paraxanthine exposure (based on $AUC_{0-t}$, $AUC_{0-\infty}$, and $C_{max}$). $AUC_{0-t}$ was increased by 88% and 10% for caffeine and paraxanthine, respectively; $AUC_{0-\infty}$ was increased by 95% and 18% for caffeine and paraxanthine, respectively; and $C_{max}$ was increased by 15% and decreased by 22% for caffeine and paraxanthine, respectively, when compared to administration of caffeine and placebo. Taken all together, CBD affects exposure of caffeine and its metabolite paraxanthine.

Conclusions

Such findings delineate an important concern for epilepsy patients and also for the wider community with the increasing legalization of marijuana. This drug-drug interaction may have implications in epilepsy patients which are not correctly monitored over the course of their treatment.

Patients that are taking caffeine-containing drugs or products should be carefully monitored over the course of their treatment with CBD to ensure toxicity from prolonged caffeine exposure does not occur.

EXAMPLE 2: LIVER SAFETY

In the above-outlined Phase 1 trial, abnormal liver chemistries were found for the subjects. This was unexpected as subjects were healthy adults receiving therapeutic equivalent doses of CBD used to treat Dravet Syndrome and Lennox-Gastaut Syndrome (1500 mg/day).

Measurements were performed at screening, on trial Days −1, 12, 18, 23, 27, and at follow-up.

Results

Figure 6:
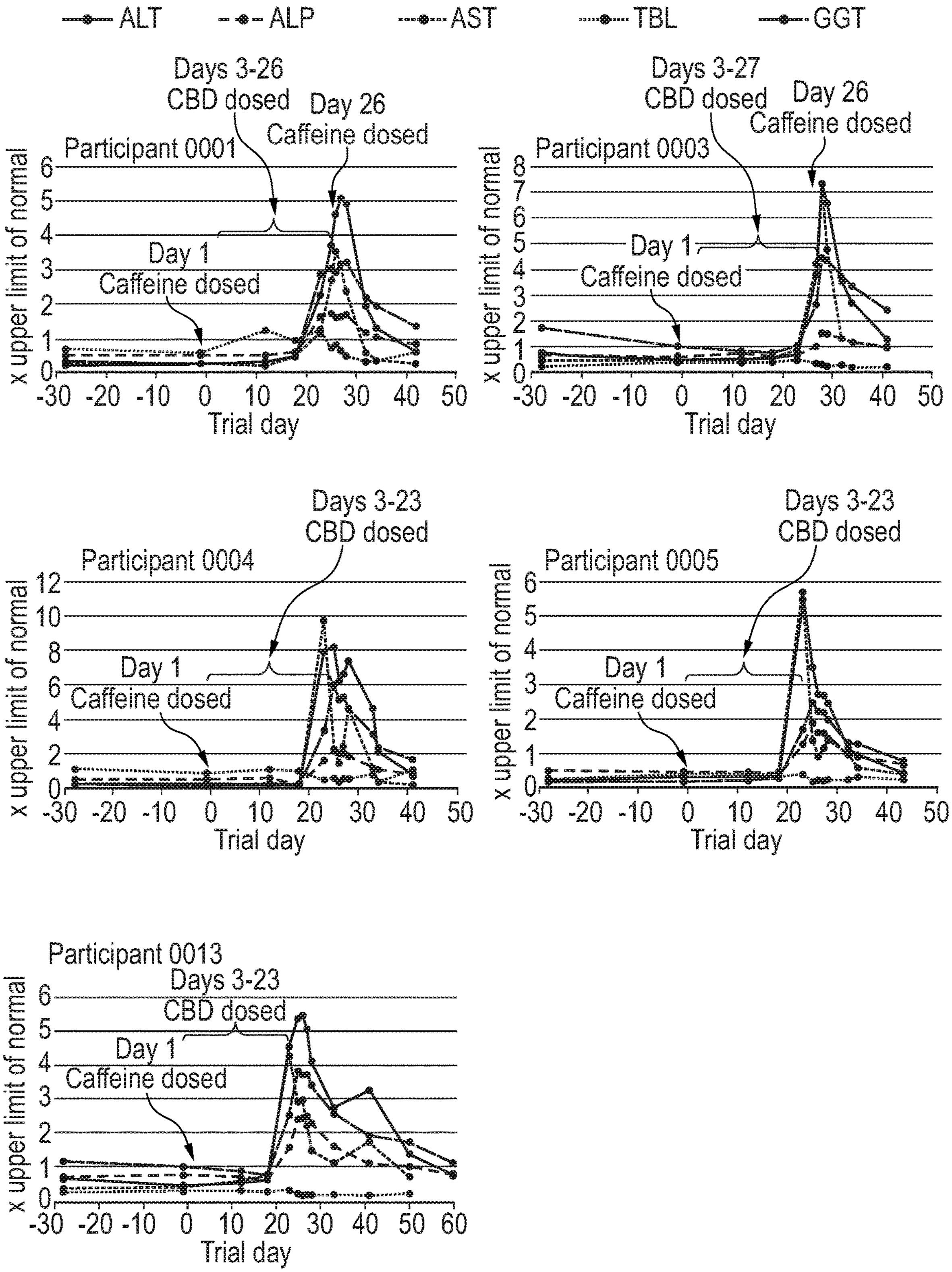
FIG. 6 shows a Graph of serial liver chemistries for the 5 participants with ALT ULN.

The most notable biochemical abnormalities were elevation in serum ALT, the related enzyme AST, and GGT. In 7 (44%) participants, peak serum ALT values were >ULN; in 6 (38%) participants the value was >2×ULN; and in 5 (31%) participants the peak ALT value was >5×ULN, the international consensus criteria for DILI (Table 6). The serial liver chemistries observed in the 5 participants with peak ALT values >5×ULN are displayed in FIG. 6.

All elevations occurred between 2-4 weeks exposure to cannabidiol, between days 18-27. Among the 6 participants with ALT elevations who were discontinued from the protocol, some had symptoms consistent with hepatitis, fever, or eosinophilia.

TABLE 6

| | Observed peak serum ALT and fold-changes from baseline value | | | | | |
|---|---|---|---|---|---|---|
| Reference ULN | >ULN | ≥2 × ULN | ≥3 × ULN | ≥5 × ULN | ≥10 × ULN | ≥20 × ULN |
| Stated ULN | 7 (44%) | 6 (38%) | 5 (31%) | 5 (31%) | 0 (0) | 0 (0) |

Conclusions

Therapeutic doses of cannabidiol administered to healthy adults can result in elevations in serum alanine aminotransferase consistent with drug-induced liver injury. Physicians should be alert to this potential effect from cannabidiol and be on the lookout for association with clinically important liver injury.

Furthermore, abnormal liver chemistries in healthy volunteers dosed with CBD at the doses used in this study have not heretofore been observed at the high rates seen in this trial (44%). As such the DDI observed between CBD and caffeine may have an impact on the DILI experienced by these patients.

It is therefore imperative that levels of CBD, caffeine, and liver enzymes (ALT, AST, and GGT) are measured in patients administered CBD who are concurrently taking caffeine either as a medication or recreationally. Caution is required to ensure DILI does not occur in these patients. Reduction of the dose of CBD, the dose of caffeine or the doses of both CBD and caffeine may be required to ensure patients liver chemistries are safe.

REFERENCES

1. Brands, B., Sproule, B., & Marshman, J. (Eds.). (1998). *Drugs & drug abuse* (3rd ed.). Ontario: Addiction Research Foundation.
2. Warzak, W. J., Evans, S., Floress, M. T., Gross, A. C., Stoolman, S. (2010). *Caffeine Consumption in Young Children*. The Journal of Pediatrics. VOLUME 158, ISSUE 3, P508-509, Mar. 1, 2011. DOI:https://doi.org/10.1016/j.jpeds.2010.11.022
3. Gillen, D. (2019). How Does Caffeine Affect CBD? https://greendoorcbd.com/blogs/news/how-does-caffeine-affect-cbd#:~:text=it's%20widely%20reported%20by%20those.feelings%20of%20anxiety%20and%20nausea,
4. Malamut, M. (2019). *I Drank CBD Coffee for a Week. Here's What It Did to My Anxiety*. https://www.healthline.com/health/mental-health/i-tried-it-cbd-coffee-anxiety#10
5. Green Roads CBD Coffee and Tea. https://greenroads.com/collections/cbd-tea-cbd-coffee?rfsn=2488702.aa938d
6. Subduction Coffee+Hemp. https://subductioncoffee.com/?afmc=2j&utm_campaign=2j&utm_source=leaddyno&utm medium=affiliate 7. Samanta (2019) "Cannabidiol: A Review of Clinical Efficacy and Safety in Epilepsy", Pediatric Neurology, Vol. 96, 2019, pp. 24-29

The invention claimed is:

1. A method of treating childhood-onset epilepsy in a patient in need thereof, comprising administering to the patient a pharmaceutical composition comprising a cannabidiol (CBD) drug substance comprising at least 98% w/w CBD, wherein the patient is taking caffeine concurrently;

wherein the dose of caffeine is reduced compared to a patient that is not taking CBD concurrently, wherein the dose of caffeine is reduced to lower than 200 mg/day.

2. The method of claim 1, wherein the dose of caffeine is reduced no more than 95 mg/day.

3. The method of claim 1, wherein the dose of CBD is about 5 mg/kg/day to about 20 mg/kg/day.

4. The method of claim 1, wherein the dose of caffeine is reduced to no more than 50 mg/day.

5. The method of claim 1, wherein the CBD drug substance comprises not more than 0.15% w/w CBDA.

6. The method of claim 1, wherein the CBD drug substance comprises at least 98% w/w CBD and not more than 1.0% w/w CBDV.

7. The method of claim 1, wherein the CBD drug substance comprises at least 98% w/w CBD and not more than 0.15% w/w Δ9THC.

8. The method of claim 1, wherein the CBD drug substance comprises at least 98% w/w CBD and not more than 0.5% w/w CBD-C4.

9. The method of claim 1, wherein the CBD drug substance comprises at least 98% w/w CBD, not more than 1.0% w/w CBDV, and not more than 0.15% w/w Δ9THC.

10. The method of claim 1, wherein the CBD drug substance comprises at least 98% w/w CBD, not more than 1.0% w/w CBDV, not more than 0.15% w/w Δ9THC, and not more than 0.5% w/w CBD-C4.

11. The method of claim 1, wherein the CBD drug substance comprises at least 98% w/w CBD, not more than 0.15% w/w CBDA, not more than 1.0% w/w CBDV, not more than 0.15% w/w Δ9THC, and not more than 0.5% w/w CBD-C4.

12. The method of claim 1, wherein the childhood-onset epilepsy is selected from the group consisting of Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

13. The method of claim 1, wherein the childhood-onset epilepsy is Lennox-Gastaut Syndrome.

14. The method of claim 1, wherein the childhood-onset epilepsy is Dravet Syndrome.

15. The method of claim 1, wherein the childhood-onset epilepsy is Tuberous Sclerosis Complex.

16. A method of treating childhood-onset epilepsy in a patient in need thereof, comprising administering to the patient a pharmaceutical composition comprising a cannabidiol (CBD) drug substance, wherein the patient is taking caffeine concurrently; and wherein the dose of CBD is in the range of about 5 mg/kg/day to about 20 mg/kg/day, and the dose of caffeine is lower than 200 mg/day.

17. The method of claim 16, wherein the CBD drug substance comprises at least 98% w/w CBD, not more than 0.15% w/w CBDA, not more than 1.0% w/w CBDV, not more than 0.15% w/w A9THC, and not more than 0.5% w/w CBD-C4.

18. The method of claim 16, wherein the childhood-onset epilepsy is selected from the group consisting of Lennox-Gastaut Syndrome; Myoclonic Absence Epilepsy; Tuberous Sclerosis Complex; Dravet Syndrome; Doose Syndrome; Jeavons Syndrome; CDKL5; Dup15q; Neuronal ceroid lipofuscinoses (NCL) and brain abnormalities.

19. The method of claim 16, wherein the childhood-onset epilepsy is Lennox-Gastaut Syndrome.

20. The method of claim 16, wherein the childhood-onset epilepsy is Dravet Syndrome.

21. The method of claim 16, wherein the childhood-onset epilepsy is Tuberous Sclerosis Complex.

* * * * *